(12) United States Patent
Wilson et al.

(10) Patent No.: US 6,274,086 B1
(45) Date of Patent: Aug. 14, 2001

(54) APPARATUS FOR NON-INVASIVE IMAGING OXYGEN DISTRIBUTION IN MULTI-DIMENSIONS

(75) Inventors: David F. Wilson; Sergei A. Vinogradov, both of Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/183,235

(22) Filed: Oct. 30, 1998

Related U.S. Application Data

(63) Continuation-in-part of application No. 08/767,158, filed on Dec. 16, 1996, now Pat. No. 5,837,865.

(51) Int. Cl.$^7$ .................................................. G01N 21/64
(52) U.S. Cl. .......................................... 422/82.08; 436/68
(58) Field of Search .................................. 600/310, 311, 600/312; 422/82.07, 82.08; 436/68

(56) References Cited

U.S. PATENT DOCUMENTS

| | | |
|---|---|---|
| 3,787,119 | 1/1974 | Rybak . |
| 3,814,081 | 6/1974 | Mori . |
| 4,200,110 | 4/1980 | Peterson et al. . |
| 4,476,870 | 10/1984 | Peterson et al. . |
| 4,752,115 | 6/1988 | Murray, Jr. et al. . |
| 4,758,814 | 7/1988 | Howng et al. . |
| 4,898,175 | 2/1990 | Noguchi . |
| 4,947,850 | 8/1990 | Vanderkooi et al. . |
| 5,012,809 | 5/1991 | Shulze . |
| 5,115,137 | 5/1992 | Andersson-Engels et al. . |
| 5,127,405 | 7/1992 | Alcala et al. . |
| 5,190,039 * | 3/1993 | Takeuchi et al. ............... 600/311 |
| 5,501,225 | 3/1996 | Wilson et al. . |
| 5,515,864 | 5/1996 | Zuckerman . |
| 5,593,899 | 1/1997 | Wilson et al. . |

FOREIGN PATENT DOCUMENTS 2132348A    7/1984  (GB) .

* cited by examiner

Primary Examiner—Jeffrey Snay
(74) Attorney, Agent, or Firm—Evelyn H. McConathy; Dilworth Paxson LLP

(57) ABSTRACT

A detection device for three-dimensional tissue oxygen measurement in animals and humans comprising an array of fiber optics effective for transmitting emitted phosphorescent light, and further comprising an array of phosphorescent detectors and an excitation light emitter, forming a matrix and effective for sequential introduction of pulses of excitation light from a plurality of sites in said matrix.

34 Claims, 11 Drawing Sheets

APPARATUS FOR NON-INVASIVE IMAGING OXYGEN DISTRIBUTION IN MULTI-DIMENSIONS

CROSS-REFERENCE TO RELATED APPLICATIONS

This application is a continuation-in-part of U.S. patent application Ser. No. 08/767,158, filed on Dec. 16, 1996, entitled PHOSPHORESCENT DENDRITIC MACROMOLECULAR COMPOUNDS FOR IMAGING TISSUE OXYGEN, now U.S. Pat. No. 5,837,865.

FIELD OF THE INVENTION

This invention relates to imaging of body portions of humans and animals via phosphorimetry, and more particularly, to optical methods for imaging oxygen pressure in human and animal tissue using oxygen-dependent quenching of phosphorescence to generate two- and three-dimensional images of oxygen partial pressure.

BACKGROUND OF THE INVENTION

As known oxygen has a quenching effect on the molecular luminescence of various chemical compounds. This effect has been exploited for imaging oxygen concentrations (partial pressure) in various body portions of humans and animals. Information about the distribution and concentration of various oxygen partial pressure in various body locales is useful as an indication of tissue health, structure, defects, abnormalities and diseases. For example, in traumatic injury, the primary threat to life is often the loss of blood and resulting hemorrhagic shock. The latter results in hypotension, under perfusion of tissue and the blood flow which does occur is abnormally distributed among and within the tissues. As a result, regions in the tissue become hypoxic or relatively devoid of oxygen, the fasculature becomes leaky, and tissue function is compromised. If the damage is sufficiently severe and/or involves essential organs, surgical repair of the traumatic injury and reinfusion of blood may not be sufficient to sustain life. Treatment of trauma victims during transit to the site where surgical repair will occur is designed to alleviate the loss of blood volume, usually by plasma expanders, in an effort to maintain blood pressure. This is believed to improve oxygen delivery to the tissue and therefor stabilize its condition until surgery can be performed. A reliable method for measuring the oxygen pressure in tissue would be an invaluable asset in the critical period between the occurrence of trauma and completion of surgery. The extent of compromise of oxygen delivery to tissue can be accurately followed, helping in such decisions as to whether intervention is necessary, the choice of treatment modality and evaluation of treatment efficacy.

For examples of oxygen mapping devices, see U.S. Pat. No. 5,593,899, which discloses methods and apparatus for imaging internal body structures of animals. The apparatus and methods disclosed in this application are directed to measuring tissue oxygenation through the skin using oxygen dependent quenching of phosphorescence. In addition, there have been additional patents directed to this technology.

U.K. patent application No. GB 2,132,348A, published Jul. 4, 1984, discloses the use of fluorescent materials to measure levels of oxygen in blood both in vitro and in vivo using a fiber optic probe or catheter.

The prior art has disclosed indwelling devices for use during measurement of various blood parameters. For example, U.S. Pat. No. 3,787,119 discloses a catheter having a microlamp and a photosensitive element and other elements including a cup-like element for use in receiving blood and providing electrical output signals by means of wires extending through the catheter.

U.S. Pat. No. 3,814,081 discloses an optical measuring oxygen saturation in blood, as well as blood pressure.

U.S. Pat. No. 4,200,110 discloses a fiber optic pH probe which includes an ion permeable membrane which encloses a guide containing solid material comprised of a hydrophilic copolymer having a pH sensitive dye attached thereto. The probe functions by optically detecting a change in color of the pH sensitive dye when excited by light. A phenol red dye is employed so that it absorbs light at a particular wavelength, with the amount of light being absorbed varying in dependence upon the pH level.

U.S. Pat. No. 4,476,870 discloses a fiberoptic oxygen partial pressure probe. This probe includes a hydrophobic gas permeable envelope which contains an adsorptive support which contains a fluorescent dye. Use of the probe for measuring partial pressure of gaseous oxygen in the bloodstream is based on the principle of dye fluorescent oxygen quenching. With the probe in place with a bloodstream, fluorescent dye is excited by light having a blue wavelength, thus causing the dye to fluoresce at a green wavelength with the intensity of emitted light decreasing (quenching) with increasing levels of the partial pressure of gaseous oxygen in the bloodstream.

U.S. Pat. No. 5,127,405 discloses a fiber optic probe incorporating a luminescent composition which is used to monitor conditions of a subject. A response light from the fiber optic probe is detected and a frequency domain presentation of the response light is derived. Characteristics of the frequency domain representation are used to derive values for luminescent lifetimes or similar decay parameters and these values in turn are translated into the values of the conditions to be sensed.

Finally, U.S. Pat. No. 4,898,175 discloses an apparatus in which an illuminating light is fed by a device emitted from the tip part of an insertable endoscope. The endoscope is inserted into a body cavity and is radiated onto a part of the body to be observed. This illuminating light, having passed through a living body tissue, is imaged by an imaging device provided outside the body. The imaging device delivers a picture image signal to a signal processing device. The signal processing device processes the signal and outputs a video signal to a display device. This device displays the image observed within the living body. See also U.S. Pat. No. 4,974,850.

In addition to the above technologies, oxygen electrodes have also been designed for transcutaneous oxygen measurements. Oxygen electrodes, in contrast to systems which are based on the oxygen dependent quenching of phosphorescence, utilize substantial amounts of oxygen. The oxygen permeability of the skin is low and oxygen consumption by the electrodes can seriously deplete the oxygen pressure at the surface of the skin, resulting in measured oxygen values which are artificially low and which are strongly dependent upon blood flow in the immediate vicinity of the electrodes. In general an oxygen electrode system must compensate by heating the skin to well above normal values in order to maximally dilate the vessels. In the phosphorescence method, the negligible oxygen consumption by the measuring system will permit the use of only one modest heating, primarily to overcome possible vasoconstriction due to depressed body temperature to assure uniform conditions among subjects. Oxygen electrodes further require calibration before each use. The calibration cannot alter with the time of measurement.

See also for example, U.S. Pat. No. 4,474,850, in which there is described a method and associated apparatus for imaging an oxygen-containing internal body portion of a host animal comprising, inter alia, adding to a body fluid of the host animal a phosphorescent composition (e.g., zinc verdin or a metal porphyrin compound) compatible with the body fluid, and in which the phosphorescence of the composition is quenchable with oxygen in the body portion, irradiating the body portion with a pulse of light at a wavelength and for a time sufficient to effect phosphorescence of the composition to be emitted as light from the body portion, scanning across the body portion to measure the decay of the emitted phosphorescence across the body portion, relating any variations in the decay measured across the body portion to variations in structure of the body portion based on oxygen contained by the body portion, and displaying an image of said body portion.

Further, in U.S. Pat. No. 5,501,225, there is described yet another method and apparatus for imaging internal body structure of humans and animals. By this method and apparatus, light focused through an epifluorescence attachment excites a phosphorescent material within a body portion or tissue, with the light emanating from the phosphorescent material being collected from outside of the tissue. However, this method and apparatus suffers from the drawback of not being convenient for isolating and measuring oxygen partial pressure of specific sections of back/portions of tissue samples.

In U.S. Pat. No. 5,593,899, there is described a noninvasive system for measuring tissue oxygen dependent upon quenching phosphorescence entailing, inter alia, a phosphorescent robe or otherwise oxygen-quenchable compound applied to the surface of a skin portion of a human or animal patient via an oxygen impermeable film placed over the probe and skin portion. This system also includes an optical head overlaying the oxygen impermeable film in which the optical head comprises a means for heating the impermeable film and probe. Also provided is a means for providing an excitation light signal for exciting the probe to permit the probe to emit phosphorescent light, and a photodiode circuit to detect the phosphorescent light emitted by the probe to provide an output signal characteristic of the oxygen partial pressure via oxygen quenching measurement of the skin portion proximate to the reflected phosphorescent signal.

Several other sensor devices are known which are useful for measuring oxygen and pH content in human and animal tissue. For example, U.S. Pat. No. 4,758,814 describes a device which is composed of an elongated flexible optical fiber containing a light sensing or light emitting end, and a light collecting and processing end. The light sensing end, which is adapted to be inserted into a human or animal body, i.e. a blood vessel, is composed of a portion of the optical fiber which is covered with a membrane, and which senses and returns light through the optical fiber to the light collecting and processing end which is, for example, a detector comprising photosensitive equipment such as a photomultiplier.

The membrane is constructed of a hydrophilic porous material containing a pH sensitive dye. Several hydrophobic microspheres are embedded in and carried by the membrane, each of which carries a fluorescent dye quenchable by oxygen. Light is supplied to the proximal end of the optical fiber and conveyed through the fiber to the membrane causing the pH sensitive dye to react, and light is thereafter conveyed back through the fiber with an intensity indicative of blood pH level. The oxygen sensitive dye also is caused to fluoresce, and transmit readable fluorescence via the oxygen quenchable dye which varies with oxygen partial pressure.

This reference thus discloses a fiber optic sensitive probe for sensing both pH and oxygen partial pressure, either simultaneously or in sequence, which is made possible by the employ of the composite membrane. As also described in this reference, the hydrophilic membrane containing the pH sensitive dye and the hydrophobic microspheres contained in the membrane which contain the oxygen quenchable dye, i.e. the two measurement vectors, can be admixed with one another the mixture deployed at the same time in the same probe to obtain their respective measurements.

In U.S. Pat. No. 5,127,405, another version of a fiber optic probe is described in which, inter alia, specialized light collecting and processing equipment is employed at one end of an optic fiber and a probe is employed at the other end for insertion into the body. This is described as an oxygen-permeable transport resin in which is embedded a luminescent composition comprising crystals of an oxygen quenchable phosphorescent material. Response light from the fiber optic probe is processed in the detection equipment by derivation of frequency domain representation, and characteristics of the frequency domain are thereafter employed to derive values for luminescence lifetimes or decay parameters, which are corrected into values of conditions to be monitored.

U.S. Pat. No. 4,752,115 discloses an oxygen sensing device which employs an optical fiber, 250 nm in diameter or small enough for insertion into veins and/or arteries, and in which one end is coated with an oxygen sensitive (oxygen quenchable) fluorescent dye which fluoresces light back, dependant upon regional oxygen partial pressure, to the other end which is adapted to receive the fluorescent light and provide an outlet for the light to go to a signal detector to provide oxygen measurement. The oxygen sensing end is made by dipping an end of the optical fiber into a solution containing an oxygen sensitive fluorescent dye, such as, tris (4,7-diphenyl-1, 10 -phenanthroline) Ru(II) perchlorate, a carrier polymer, such as, polyvinyl chloride and a plasticizer dissolved in, for example, THF. The plasticizer is said to be necessary for a fast response and high sensitivity. The oxygen sensing end can also include a gas-permeable sleeve about the optical fiber.

Another fluorometric oxygen sensing device is described in U.S. Pat. No. 5,012,809 which employs a fluorometric sensor constructed with silicone polycarbonate bonded to one or more plastic fiber optic light pipes using polymethylmethacrylate glues.

U.S. Pat. No. 4,476,870 discloses a fiber optic probe for implantation in the human body for gaseous oxygen measurement in the blood stream. The probe employs oxygen quenchable dye fluorescence, and uses two 150 $\mu$m strands of a plastic optical fiber which end in a tubular envelope packed with fluorescent light-excitable dye placed on a porous absorptive particulate polymeric support. The tubular envelope is made of a hydrophobic, gas-permeable material.

U.S. Pat. No. 4,200,110 discloses a fiber optic pH probe employing an ion-permeable membrane envelope enclosing the ends of a pair of optical fibers, with a pH sensitive dye indicator composition disposed within the envelope.

U.S. Pat. No. 3,814,081 describes another variant of an optical measuring catheter for measuring the degree of oxygen saturation in blood using an illuminating fiber optical system and a light receiving fiber optical system, both of which are arranged along side of each of other, and both having forward ends adapted to be inserted together into the organ of a living body to detect illumination of from 600 to 750 nm to measure blood oxygen concentration. This method does not rely on oxygen quenchable phosphor/fluorophor compounds, but instead employs direct measurement of light absorption of Hb vs. $HbO_2$ at specific wave lengths.

In another example, U.S. Pat. No. 3,787,119 describes a multiple photometer device mounted in a catheter, which utilizes at least two associated photosensitive cells to measure physical and chemical characteristics of blood in vivo.

Finally, in co-pending U.S. application Ser. No. 08/767, 305, now U.S. Pat. No. 5,830,138, the entire disclosure which is incorporated herein by reference, there is described an improved optical probe for use in measuring blood and tissue oxygen partial pressure and pH ($CO_2$) measurements. In this method and apparatus, a probe is provided for use in measuring blood and tissue oxygen partial pressure and pH ($CO_2$) measurements in humans and animals, which comprises a fiber optic means effective for transmitting phosphorescent and/or fluorescent light, an oxygen and/or pH probe means situated at one end of the fiber optic means which comprises a portion of the fiber optic means enclosed by a gas permeable membrane, a reservoir means which compromises a solution of an oxygen-quenchable phosphorescence-emitting compound and/or fluorescent-emitting compound situated between the gas permeable membrane end fiber optic means, and further comprising at the other end of the fiber optic means a phosphorescent and/or fluorescent light detection means to receive light from the fiber optic means, to measure tissue and blood oxygen and/or pH. The device further comprises an excitation light-emitting means to provide light to the phosphorescent and/or fluorescent emitting compounds.

In other embodiments of this invention, the oxygen-quenchable phosphorescence-emitting compound and/or fluorescence-emitting compound (hereinafter "phosphor" and fluorophor" respectively) is dissolved in a solvent having substantially the same refractive index as the fiber optic means, and/or the fiber optic means portion comprising the probe means has at least a portion thereof etched or is otherwise provided with a plurality of grooves or depressions to provide additional angled surfaces to aid in scattering excitation light outward into the phosphor and/or fluorophor-containing medium to the fiber optic means, and thereafter back to the light detection means. In a further embodiment the probe means contains a plurality of grooves or depressions, a portion of which contain an oxygen-quenchable phosphor for oxygen measurement and a portion of which contain a fluorophor for pH ($CO_2$) measurement.

While the above-described methods and apparatus for imaging oxygen partial pressure in tissue using oxygen-dependent quenching of phosphorescence are capable of generating two- dimensional images of oxygen pressure, three-dimensional information has been unobtainable, or relatively difficult to obtain. Such information would be highly beneficial as a diagnostic tool, and in many cases pivotal in quickly, accurately and precisely diagnosing many heretofore difficult to diagnose maladies.

SUMMARY OF THE INVENTION

The present method and apparatus provides both two- and three-dimensional images using an approach which takes advantage of novel technology and phosphors.

In accordance with the present invention, oxygen measurements in tissue take advantage of novel phosphors which absorb and emit light in the near infra red region of the spectrum for which both excitation and emission light can pass through relatively great thicknesses (several cm) of tissue. Further, in accordance with this invention, light-emitting diodes are used for excitation of the phosphorescence, thereby taking advantage of their ability to provide a bright monochromatic light source which can easily be modulated at the required frequency and with the desired waveform.

In this inventive process and apparatus, phosphorescence emission is measured using a specially constructed matrix of light guides and/or phosphorescence detectors which allow precise and sequential introduction of pulses of excitation light from several different sites in the matrix. For each injection of a pulse of excitation light at a site, phosphorescence detectors collect the emitted phosphorescence and determine: (a) the total phosphorescence signal amplitude; (b) the histogram of the distribution of oxygen pressures, and (c) the fraction of the phosphorescence signal due to phosphor in regions with oxygen pressures less than selected values. In accordance with this invention, it has been found that the combination of these measurements unexpectedly enables and/or enhances the expedited calculation of the three- dimensional image of the distribution of hypoxic regions in the tissue.

This invention is more fully illustrated and described by the following detailed description with reference to preferred embodiments and figures.

DETAILED DESCRIPTION OF PREFERRED EMBODIMENTS

As set forth hereinabove, the present inventive method and apparatus employing novel technology in the form of oxygen-quenchable phosphorescence-emitting compounds ("phosphors") and apparatus to monitor oxygen-quenching of phosphorescence provides both a two- and three-dimensional quick and reliable imaging approach to measure blood and tissue oxygen partial pressure, or concentration.

As further set forth above, two-and three-dimensional oxygen imaging of tissue is accomplished in the present inventive method by measuring phosphorescence emission of the oxygen-quenchable compounds in an apparatus comprising a matrix of light guides and/or phosphorescence detectors to allow precise and sequential introduction of pulses of excitation light from a plurality of sites in the matrix. Further in accordance with this invention, for a given injection of a pulse of excitation light at a site, a phosphorescence detector collects the emitted light and determines one or more measurements selected from the group consisting of, (a) the total phosphorescence signal amplitude; (b) the histogram of the distribution of oxygen pressures, and (c) the fraction of the phosphorescence signal due to the phosphor in regions with oxygen pressures less than selected values (for example, less than 40% and less than 10% of the primary value, i.e., if the primary value is 35 torr, the fractions less than 14 torr and less than 3.5 torr would be calculated) to unexpectedly enhance and expedite the calculation of a three-dimensional image of the distribution of hypoxic region in a sample.

The Optical Matrix

The matrix of points for excitation light and emission collection are preferably arranged such that for each site of excitation there are collection sites at selected intervals for a distance appropriate to the required spatial resolution. For example, the matrix can be designed to detect regions of relative hypoxia down to 1 mm in diameter in breast tissue. In this example, the excitation sites may be placed at intervals of 0.8 cm and the matrix shaped to fit the breast. On the other hand, for the evaluation of the larger regions of hypoxia which might occur in the brain of neonates, the excitation sites may be placed at 2 cm intervals and the matrix shaped to fit the head. A possible design for the matrix is shown in two dimensions in FIG. 1.

Excitation and Phosphorescence Measuring Matrix

Figure 1:
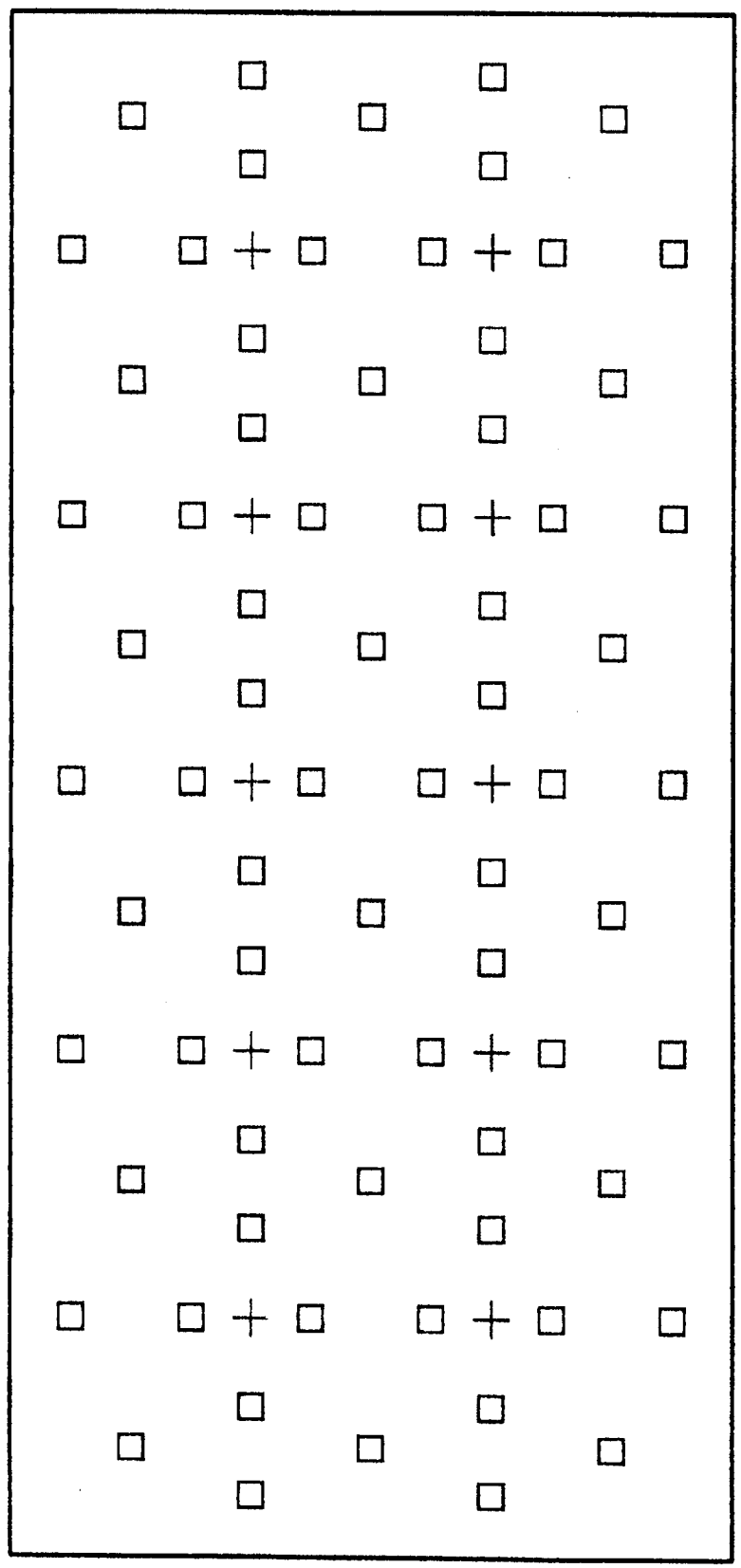
FIG. 1 illustrates a matrix array of detection and excitation points for three-dimensional oxygen imaging in accordance with the present invention.

In FIG. 1, the points of excitation preferably using optical fibers are indicated with an E and the sites for measuring phosphorescence emission are indicated with D. In a preferred configuration, the excitation fibers are from approximately 10 $\mu$m to approximately 1000 $\mu$m in diameter, and are more preferably 125 micron graded index fibers, and the emission sites may be from approximately 100$\mu$ to approximately 4 mm in diameter with approximately 2 mm diameter light collection sites being most preferred and also preferably covered with an optical filter to exclude the excitation light while passing the longer wavelength phosphorescence emission prior to applying excitation light. A phosphor solution is injected into the systemic blood in an area with tissue having suspected regions of hypoxia and measured for oxygen concentration via infusion of excitation light and measurement of phosphorescent emission. While not critical to this invention, phosphor solutions preferably used are in amounts ranging from about 0.1 to about 10 mg/kg body weight.

In a preferred mode of operation in accordance with this invention, phase modulation is used to measure phosphorescence lifetime. While not critical to the invention, a laser diode is modulated, for example, preferably at from about 200 to about 20,000 Hz for current phosphors, and the light conducted to the inventive matrix with 125 micron fibers. The phosphorescence collection sites are approximately 2 mm in diameter. The time necessary to make the phosphorescence lifetime measurements may be about 2 seconds per excitation injection site. As excitation light is injected at one of the sites, the phosphorescence emission is measured at all of the collection sites for which sufficient intensity is available to give an appropriate signal to noise, which are preferably all sites within about 5 cm of the excitation site using the electronic scheme diagramed below in FIG. 2 (to be further explained hereinbelow). Thus, for each pulse of excitation light, the phosphorescence decay characteristics (oxygen distribution information) is measured at a plurality of different sites in the matrix, for example, up to 50 or more. The phosphorescence decay data for a sequence of pulses of excitation light, one at each of the excitation sites, can be collected in a relatively short time, for example, less than about 4 minutes. Following data collection, the digitized data is resolved into the underlying distributions of phosphorescence lifetimes (and thereby oxygen concentrations) and their relative signal strengths (related to their relative tissue volumes). This allows the apparent tissue volume at each oxygen pressure (oxygen histogram) to be determined for each excitation site and detection site pair (one E and one D site, respectively, as described more fully hereinbelow) and such data then used to generate a three-dimensional map of oxygen distribution in the tissue volume. Such method of determination therefore utilizes oxygen distributions measured from a plurality, for example, from one hundred to several thousand positions about the tissue volume of interest.

As is known, the intensity of the excitation light decreases with increasing distance from the excitation site and the intensity of the phosphorescence decreases with increasing distance from the point of emission. Thus, the position of any hypoxic region within the tissue can be calculated from a combination of the total phosphorescence signal strength, which is a measure of distance from the excitation source, and the fraction of the total phosphorescence signal generated by the hypoxic tissue volume, a measure of the size of the hypoxic volume and its distance from both the excitation and emission sites. The hypoxic fraction will therefore increase with closeness to the excitation site and with closeness to the emission site. The positions of all of the excitations and emission sites within the matrix can thus be accurately known. Their relative positions in three dimensional space can thus be directly calculated as can position and size of the hypoxic volume. The calculations of the three-dimensional image of oxygen distribution, particularly the positions and sizes of any regions of relative hypoxia, requires a relatively short period of time, such as less than about 3 minutes.

Again, while not critical to the invention, in a preferred embodiment, imaging apparatus employed in this invention may comprise an instrument comprising a central microcomputer with, for example, a 300 Mhz pentium processor, 64 MB RAM and a high resolution display. This is connected to a series of 5 digital signal processors (DSP) units, each consisting of a central RISC processor, two A/D units capable of 500 kHz, 16 bit operation (for 10 channels of phosphorescence data), memory and ROM. The DSP units are responsible for digitizing and analyzing the phosphorescence data and transmitting this data to the central microcomputer for calculation of the final oxygen distribution images. The excitation light is provided by a plurality of laser diodes, for example 5, each coupled to a 125 micron fiber. These fibers lead to 4-way optical switches to allow automatic switching, providing excitation light to a plurality of fibers, e.g., excitation sites. The phosphorescence collection sites are preferably amplified photodiodes built directly into the optical matrix, each with 4 mm$^2$ active surface area and covered with an appropriate optical filter to isolate the phosphorescence from the excitation light. As these photodiodes may operate with only 5 V power supplies, the electrical hazard is minimal. Alternately, the light can be collected with optical fibers and carried to photodiodes mounted in the DSP unit, resulting in a measurement matrix being electrically completely isolated, as shown in the block diagram below in FIG. 2.

DSP units suitable for use in the inventive apparatus needs only a few surface-mounted chips for real time measurements of signal amplitude and phase relative to the output of the laser diode. Each DSP unit preferably includes a high speed A/D chip, such as a 500 kHz, 16 bit A/D, a high speed RISC processor, such as 60 MHz TMS320C31, digital filters, memory and ROM to contain the data processing programs, etc. Each DSP unit is able to run extensive internal diagnostics to assure its own optimal operation. In addition, the digital output can be directly transmitted to the central control unit.

The optical head is preferably connected to the instrument pack by flexible optical fibers approximately 24" long. A 125 $\mu$m fiber can carry the excitation light from the laser diode and a 4 mm$^2$ area of 50 $\mu$m fibers may collect the phosphorescence emission. The excitation and emission areas are preferably separated by a plurality of distances as shown in FIG. 1. This separation can be easily altered and the final values will be chosen on the basis of routine experimental performance. The rest of the optical head may be flexible skin compatible material which does not transmit near infra red light and can be taped in place.

Utilizing the above combination of laser diodes, photodiode light sensors, microcircuits and novel phosphors, to be discussed more fully hereinbelow, a phosphorescence lifetime measurement instrument is provided which is both very small and highly reliable. The phosphorescence lifetime and signal strength data is transmitted to a remote data handler for final analysis.

Block Diagram of a Digital Signal Processing Unit

Figure 2:
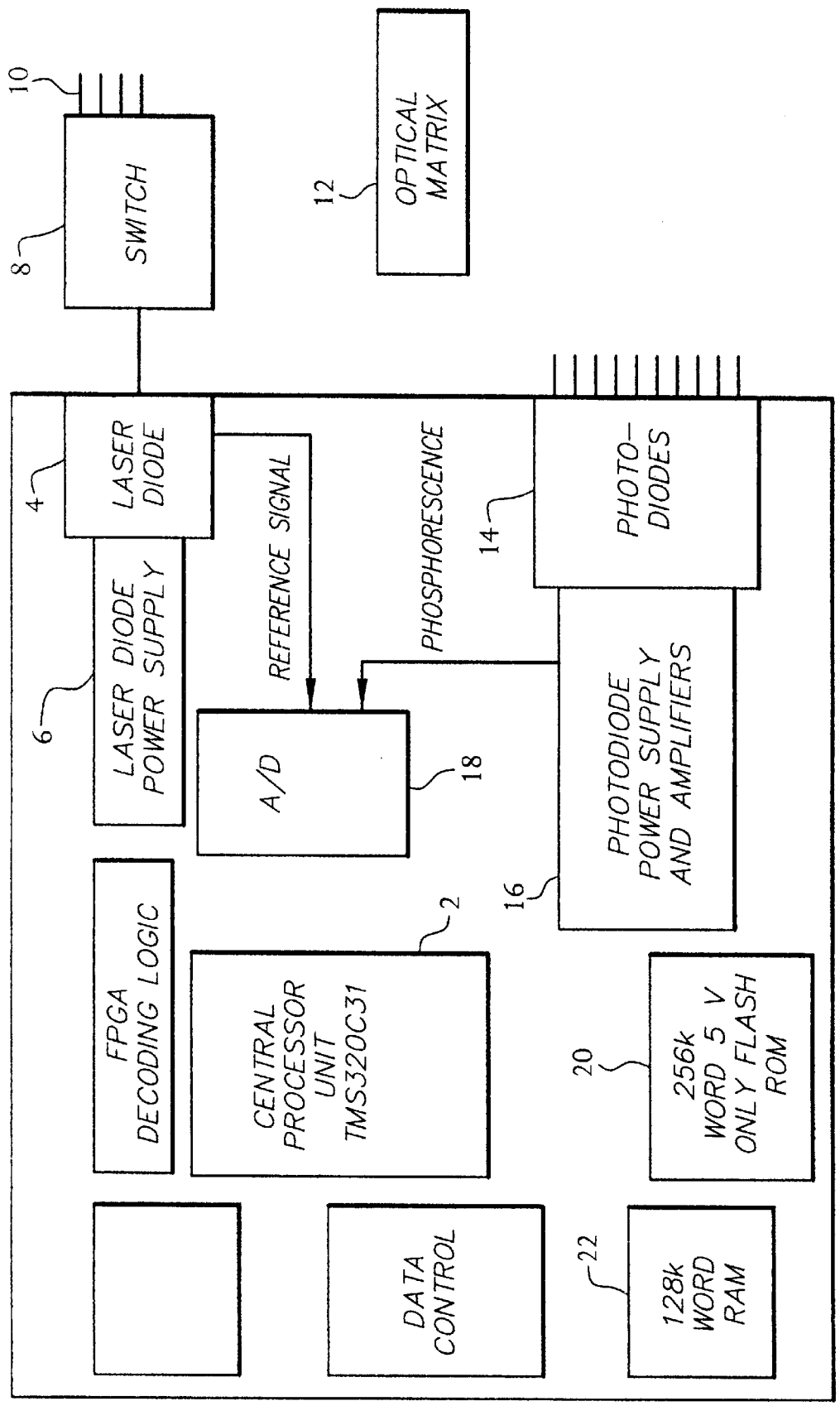
FIG. 2 illustrates a block diagram of a digital signal processing unit (DSP) for use in the invention in generating three-dimensional oxygen imaging.

In FIG. 2, there is shown a block diagram of a preferred digital signal processing unit for use in accordance with this invention. As shown, the DSP comprises a central RISC processor unit 2 (60 Mhz TMS320D31), a high speed analog-to-digital (A/D) chip 4 500 kHz, 16 bit A/D. The central processor computes a table of values for the laser diode current and these values are processed by a 16 bit digital-to-analog (D/A) to provide the desired time dependence of the laser diode light output (single or multiple frequencies). The light is coupled into a 125 micron fiber to a 1×n switch that can selectively direct the light to a plurality of excitation sites E1, E2, E3, - - - En. When E1 is illuminated the phosphorescence is collected from a plurality of detection sites D1, D2, D3, - - - Dn. The switch then directs the excitation light to E2 and the process repeated. This continues until all of the excitation sites have been illuminated. For each excitation site the signals from detectors D1 through Dn are digitized and stored in memory by a DSP unit. The phase and amplitude relative to the excitation light of each is determined by the DSP and this data sent to the central computer for further analysis. Since each DSP unit can evaluate data from 2–6 channels in "real time", there need be only one DSP processor for each 2–6 detectors. In a non-limiting illustrative example, the requirements for a 20×20 square matrix (400 measurements per image) are one laser diode with a 1×20 switch, 20 bundles of collection fibers with associated detector units, and 4–5 DSP units and a central computer. The data collected is 20 measurements for each excitation site, providing a total of 400 measurements per image. For the matrix shown in FIG. 1, there would be 10 excitation sites and 66 detection sites or 660 measurements per image.

Turning now to FIG. 2 in detail, there is shown an example of a preferred configuration of A DSP unit for use in this invention. The components shown comprise a central processor unit, laser diode, laser diode power supply, switch, optical matrix, photodiodes, photodiode power supply and amplifiers, A/D, 256 k Word flash ROM, and 128 k Word SRAM.

The central digital signal processor (DSP) 2 handles all of the data processing, including calculation of the tables of values used for driving the laser diode light output in the selected mode (single or multiple frequencies), and processes the digital phosphorescence intensity data from the A/D unit. Suitable DSPs include the currently available TMS320C31 and ADSP 21000 series processors. The laser diode 4 provides the phosphorescence excitation light appropriate to the phosphor, such as 635 nm light for tetrabenzoporphyrin probes to be more fully discussed below. The laser diode power supply 6 provides current to the laser diode which is modulated under control of the DSP to give the selected light output pattern appropriately for determination of phosphorescence lifetimes and lifetime distributions. The optical switch 8 allows light from a single laser diode, coupled to a small optical fiber (preferably 100 to 200 microns) to be selectively directed into any one of several other fibers 10 (controlled by the DSP) for conduction to the optical matrix 12. The optical matrix determines the relationships of the several excitation sites and the several detection sites selected for analysis (see FIG. 1). The photodiodes 14 are sensitive light detection units (photodiode, avalanche photodiode or photomultiplier), one for each detection site, which detect the phosphorescence and convert the light intensity to electrical current or voltage for amplification and digitization. The photodiode power supply and amplifiers 16 condition the photodiode output to allow optimal input to the A/D 18 for digitization. The A/D unit digitizes the signal from the photodiode amplifiers with a sampling frequency (such as 48 kHz) and accuracy (such as 16 bits) that provides appropriate resolution of the light modulation frequencies. The A/D may digitize the signal from more than one photodetector if it has sufficient capacity (e.g., a 200 kHz A/D could digitize 4 signals each at 50 kHz). The ROM 20 (read-only memory) contains the programming necessary to initiate operation of the DSP when it is turned on. The RAM 22 is used for the program that operates the DSP and provides memory for data processing by the DSP. The larger the calculation carried out by the DSP the greater the requirements for RAM. In some configurations, this could be as large as several MB.

Other parts of the DSP unit illustrated in FIG. 2 are the communication chips, such as a serial port for communication with the central computer, and a digital to analogue converter (D/A) for controlling the laser diode current.

EXAMPLE

Determination of Tissue Oxygenation in 3-Dimensions

Figure 3:
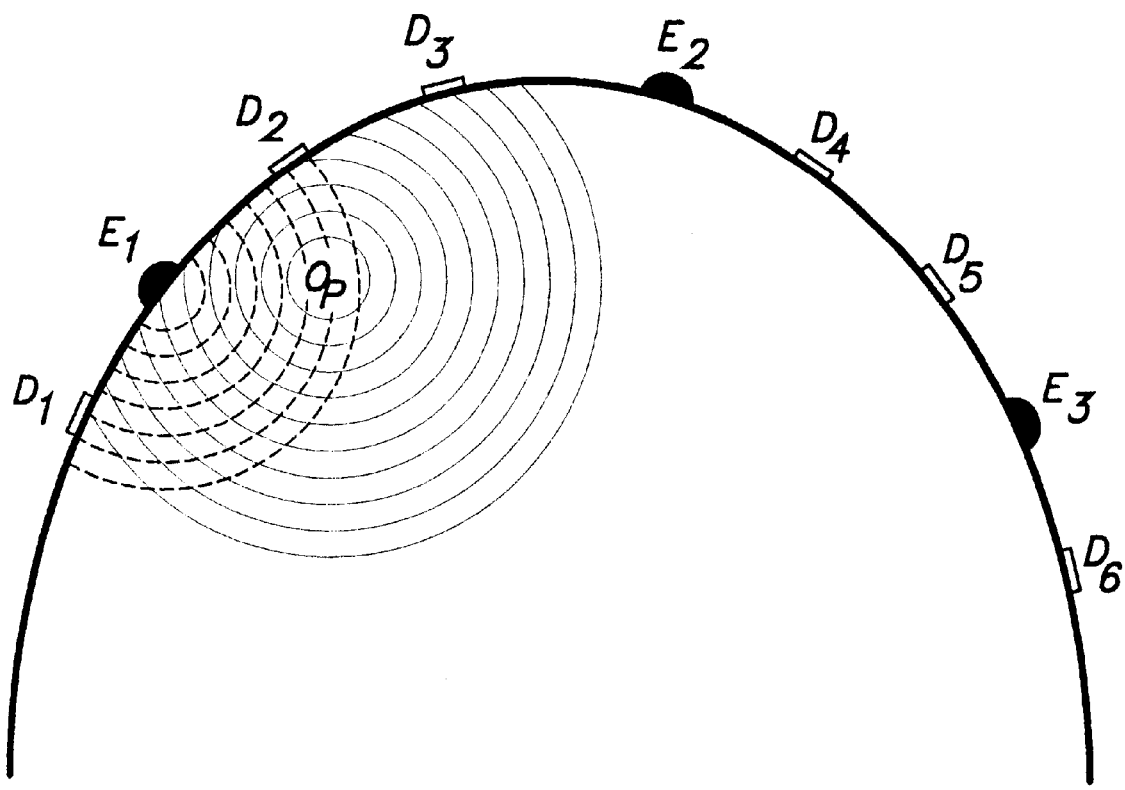
FIG. 3 illustrates a two-dimensional section of a three-dimensional tissue volume with the applied inventive matrix array of detection and excitation sites.

As shown in FIG. 3, there is a 2-dimensional sectioriwof a 3-dimensional tissue volume with the inventive measurement matrix designated by the array of $D_1$, $E_1$, $D_2$, $D_3$, $E_2$, $D_4$, $D_5$, $E_3$, $D_6$, with designating a site for detection of phosphorescence ad E designating a site of excitation, fitted to the tissue surface with the designations of 1, 2, 3, - - - n being the number assigned to that particular site. As mentioned above, this array is fitted to or placed on, incorporated or otherwise associated with a material that is preferably skin-compatible, and which can be applied or fitted to an area for oxygen measurement. Tissue is a highly scattering medium with low absorbance in the near infrared. Light, both excitation and phosphorescence, diffuses through the tissue with attenuation of approximately 90% per cm linear distance traversed through the tissue. In this treatment, the attenuation is fitted with an exponential series; the form of the fitting equation is not critical to the invention and is merely relevant to the computation approach.

$E_i$=points of introduction of excitation light where i is the position (i varies from 1 to n)

P=a tissue volume with local hypoxia and therefore longer lived phosphorescence.

$D_i$=light (phosphorescence) detection ports.

Without wishing to limit this invention to any particular theory, it is thought that as the excitation light travels outward through the tissue, it will be both scattered and absorbed, decreasing in intensity as the distance from the point of introduction increases. As light passes through tissue it is both scattered by the membranes and other particles and absorbed by tissue pigments, a process which results in an exponential decrease in intensity with increasing thickness of tissue. There are several methods in use for calculating the attenuation of light as it passes through tissue, including without limitation, empirical curve fitting, Monte Carlo calculations of diffusion, and Beer-Lambert law altered to include the increase in light path due to scattering. Any of these techniques can be successfully used to describe light attenuation in tissue. One method for expression of this attenuation can be represented as follows in Equation (1):

$$E_j = E^o(1 - adi - bd_i^2 - cd_i^3 - dd_i^4) \tag{1}$$

where $E^o$ is the initial excitation intensity, $E_j$ is the intensity at position j within the measured volume, a, b, c, d, are constants and $d_i$ is the distance from the site $E_i$.

The phosphorescence arising from a volume of tissue ($P_i^o$) is proportional to the concentration of phosphor (C), its extinction coefficient ($\epsilon$), the quantum efficiency (Q), Ei and $V_i$, where $V_i$ is the relative volume of tissue measured for that excitation-detection pair, as represented below in Equation (2):

$$P_i^o\ C\epsilon QE_iV_i \tag{2}$$

For most tissue the phosphor is nearly uniformly distributed and $C\epsilon$ and $V_i$ can be considered constants, as represented below in Equation (3).

$$P_i^o = kEiQ, \tag{3}$$

where k=F(c, $\epsilon$, $V_i$) and the quantum efficiency is a function of the local oxygen pressure.

As the phosphorescence travels from the position $P_i$ to each detector, it is attenuated such that, $$P_i = P^o{}_i((1 - ad_k^1 - bd_k^2 - cd_k^3 - dd_k^4) \tag{4}$$

where $d_k$ is the distance from $P_i$ to $D_i$.

For any given site of introduction of excitation light, the values related to excitation light are the same for every detection site and only equation (4) needs to be considered. Any two detector sites can be used to triangulate the position of the phosphorescent volume $P_i$. Given there will be several detector sites at different positions about the perimeter of the volume, an appropriate computer program may be used to minimize the differences in the values of a, b, c, and d required for best localization of Pi. A complete three-dimensional (3-D) map of phosphorescence distribution can therefore be generated from measurements using a single point ($E_1$) of excitation. The resolution of the map improves rapidly, however, as solutions for additional excitation sites are included.

For each additional site of injection of excitation light the position(s) of the hypoxic regions remain in the same position in 3-D space, this being achieved through equation (1) which corrects for the change in $E_j$ (excitation intensity)

Oxygen Dependent Quenching of Phosphorescence as a Preferred Method for Evaluating Tissue Oxygen dependent quenching of phosphorescence is the preferred method for evaluation of tissue oxygenation in three-dimensions in accordance with this invention.

Phosphorescence quenching is an accurate measure of oxygen pressure over a wide range, with particular advantage over other methods for oxygen measurement in the lower range of physiological oxygen pressures (e.g., 10 Torr). The response time is only a few msec, even at low oxygen pressures, and rapid measurements are possible at all oxygen pressures. Phosphorescence quenching has been effectively used, for example, to measure the oxygen dependence of the respiration of suspensions of mitochondria (WILSON et al. 1988) intact cells (ROBIOLIO et al. 1989); RUMSEY et al. 1990) where it is the only available method with the necessary combination of rapid response time and sensitivity at low oxygen concentrations. Optical quenching measurement is an optical method which is non-invasive except for the necessity for injecting phosphorescent probe (oxygen-quenchable compound or phosphor), into tissue to be measured for oxygenation. It is the only available oxygen measuring system capable of non-invasive, quantitative determination of the oxygen pressure in the vasculature of tissue in vivo. Phosphor dissolved in the blood provides an excellent measure of the oxygen pressure within the vasculature, particularly the microvasculature tissue. Thus, the phosphorescence measurements provide a rapid and accurate measure of the degree of hypoxia in the tissue in either hypoxic or hemorrhagic hypotension.

Quenching of phosphorescence by oxygen occurs by well understood principles and the relationship of phosphorescence of oxygen pressure can be expressed in the form of a simple linear equation. The measured phosphorescence intensity or lifetime may be converted to oxygen pressure using the Stem-Volmer relationship shown below in Equation (5):

$$T°/T = 1 = k_Q T° PO2 \quad (5)$$

where T° is the phosphorescence lifetime in the absence of oxygen, and T is the phosphorescence lifetime at oxygen pressure $PO_2$. $k_Q$ is a constant related to the frequency of quenching collisions between the probe molecules in the triplet state and molecular oxygen and is a function of the diffusion constants for probe (phosphor) and oxygen, temperature and phosphor environment. Measurements have verified that the phosphors (or probes) used in the present invention accurately follow Equation (5).

No known agents in blood, other than oxygen, affect the measured phosphorescence lifetime. Phosphors for use in humans and animals in this invention are preferably synthetically encased in a molecular environment which replaces binding to albumin. The final molecule preferably was a molecular weight (approximately 4,0000–7,000 Daltons) and other properties such that it is excreted in the urine without modification. This means the micro environment of the phosphor is constant and the calibration constants measured in vitro are valid for measurements in vivo. Moreover, once the values of $k_Q$ and T° have been determined, these values can be used indefinitely, e.g., the calibration is only dependent on the chemical structures involved and not the measuring apparatus or the preparative procedures. Values of $k_Q$ and T° determined in the laboratory are shown to be equally valid for measurements in vivo, eliminating the need for calibration in the field.

There is no evidence for toxicity of the phosphors (probes) used in the present invention including the novel phosphors absorbing in the near infrared region of the spectrum as discussed more fully below. For example, 5 mg. of Green 2W (about 150 mg/kg) have been injected per mouse into 6 mice with no evidence of toxicity in the following 10 days. In contrast, even with conventional instruments less than 0.3 mg/mouse (10 mg/kg) is sufficient for imaging oxygen pressure, using even transillumination, and measurements with light guides require less than 0.1 mg/mouse. Further increase in sensitivity with the inventive apparatus will lower the phosphor requirement to less than about 0.3 mg/kg body weight. The possibility of phosphor toxicity is completely eliminated in the present invention by designing it to remain in the blood until excreted through the kidney, chemically unchanged; a process requiring only a few hours.

Phosphorescence lifetime is independent of phosphor concentration throughout the range utilized for measurements in vivo. The calibration parameters for many of the phosphorescent oxygen probes, such as Green 2W are also completely independent of pH in the physiological range, and only small temperature dependence need be considered.

Phosphorescence lifetime measurements are independent of the absorbance or fluorescence of other chromophores which may be present in the system. Weakly absorbing chromophores (in the near infrared), such as hemoglobin and myoglobin, which are present do not change absorbance during a phosphorescence decay (approximately 1 msec), and therefore cannot affect the measured phosphorescence lifetimes. Fluorophors, if present, have lifetimes of less than 100 nanoseconds and therefore are easily separated from phosphors which optimally have lifetimes of greater than 5 microseconds.

The oxygen-quenchable phosphorescent compound (probe) or hereinafter "phosphor" employed in this invention is preferably a material having a substantial sensitivity to oxygen, i.e. phosphorescence with high quantum yields at room temperature ($\geq 2\%$); and a suitable phosphorescent lifetime, preferably on the order of from about 0.1 to about 1 m sec.

A novel class of phosphors suitable for oxygen measurements which have the above desirable qualities is now available, and are preferably used as the phosphors of choice in this invention. These phosphors are described in detail in VINOGRADOV et al., "Metallotetrabenzoporphyrins. New Phosphorescent Probes for Oxygen Measurements", *J. Chem. Soc., Perkin Trans.* 2:103–111 (1995) and in copending application Ser. No. 08/137,624, filed Oct. 15, 1993, the entire disclosures of which are incorporated herein by reference. These phosphors are metallo complexes of, for example, extended porphyrins, such as Pd or Pt tetrabenzoporphyrins (PdTBP) tetranaphthaloporphyrins (PdTHP), and tetraphenyltetrabenzoporphyrins (PdTPTBP) and derivatives thereof, which are preferred for use in this invention. These compounds can be represented by the general formula,

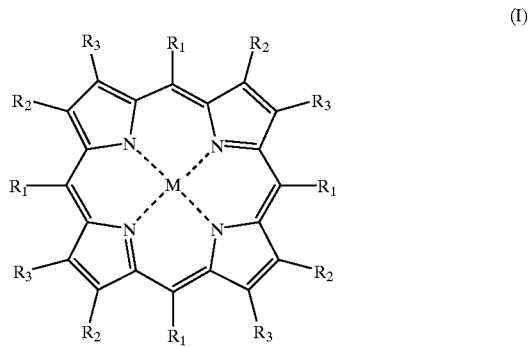

(I)

where $R_1$ is substituted or unsubstituted aryl; $R_2$ and $R_3$ are independently hydrogen or are linked together to form substituted or unsubstituted aryl; and M is $H_2$ or a metal.

As is apparent to those skilled in the art, when $R_2$ and $R_3$ are linked together to form an aryl system, the aryl system is necessarily in a fused relationship to the respective pyrrole substrate.

M is preferably a metal selected from the group consisting of Zn, Al, Sn, Y, La, Lu, Pd, Pt and derivatives thereof. Non-limiting examples of suitable metal derivatives include LuOH, YOH, AlOH and LaOH.

In certain preferred embodiments, the compounds of the present invention are tetrabenzoporphyrin (hereinafter "TBP") compounds, which correspond to the compound of formula I above wherein vicinal $R_2$ and $R_3$ groups are linked together to form benzene rings which are fused to the respective pyrrole rings. Also preferred are tetranaphthaporphyrin (hereinafter "TNP") and tetraanthraporphyrin (hereinafter "TAP") compounds wherein vicinal $R_2$ and $R_3$ groups are linked together to form naphthalene and anthracene ring systems, respectively. As with the fused benzene rings, the naphthalene and anthracene ring systems are fused to the respective pyrrole rings.

Unless indicated otherwise, or unless apparent from the disclosure, further references herein to "TBP" compounds is understood to refer also to TNP and TAP compounds.

Preferred TBP compounds have the following formula

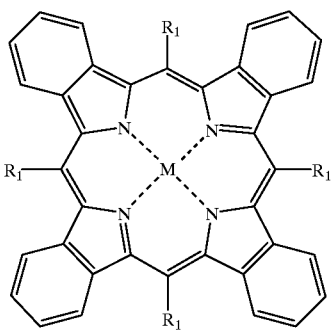

(II)

wherein $R_1$ and M are as defined above. Particularly preferred TBP compounds are metallotetrabenzoporphyrin (hereinafter "MTBP") compounds where M is a metal or metal derivative as described hereinbefore.

TBP compounds of formula II above can be synthesized, for example, by template condensation of potassium phthalimide with sodium acetate (or sodium phenylacetate) in the presence of zinc acetate (See, for example, V. N. KOPRANENKOV et al., *J. Gen. Chem.* (Russ), Vol. 51(11), pp. 2165–68 (1981) and V. N. KOPRANENKOV et al., *J. Org. Chem. of USSR*, Vol. 15(3), pp. 570–75 (1979)) as described in the following equation:

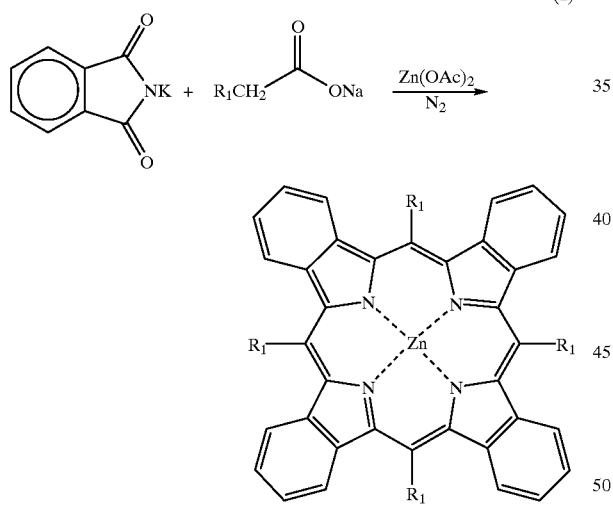

(1)

where $R_1$ is defined as above. The reaction mixture is preferably heated to a substantially elevated temperature, for example, about 360° C., for about 40 minutes. Zinc acetate in this reaction is reportedly replaceable with Zinc benzoate. See K. ICHIMURA et al., *Inorgan. Chem. Acta,* 182:83–86 (1991).

The product from the reaction of equation 1, zinc tetrabenzoporphyrin (hereinafter "ZnTBP"), is reduced to the dihydro product by heating in a mixture of acetic and phosphoric acids as described in the following equation:

(2)

wherein $R_1$ is defined as above. Preferably, the acetic and phosphoric acids are mixed in a ratio of about 1:3 and the reaction mixture is heated to about 80° C. The reaction is substantially complete in about 2 hours.

The dihydrotetrabenzoporphyrin product from the above reaction (hereinafter "$H_2$TBP"), can be purified by flash chromatography on an alumina ($Al_2O_3$) column. Metal insertion can be carried out in an imidazole melt as set forth in the following equation:

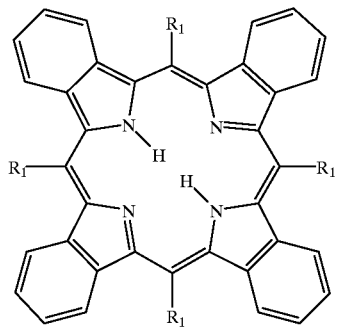

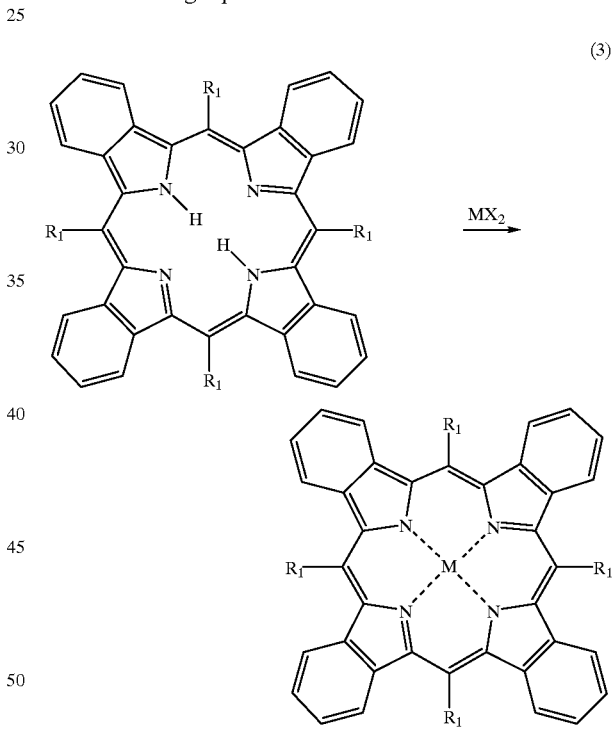

(3)

wherein $MX_2$ is a source of metal ions and preferably corresponds to chlorides, bromides and acetates of metals. Metal acetates are preferred sources of metal ions as compared to the corresponding halides. Palladium acetate (Pd(OAc)$_2$) is particularly preferred and has been shown to provide approximately 99% conversion to the metal complex in refluxing tetrahydrofuran (THF). The reaction of equation 3 is preferably conducted at elevated temperatures, for example, temperatures greater than 100° C. Preferably, the reaction is conducted at a temperature of about 200° C., and the reaction is substantially complete after about 1 hour.

Particularly preferred among the TBP compounds are the compounds of formula II above where at least one of $R_1$ is substituted or unsubstituted phenyl. These compounds are referred to hereinafter as phenyltetrabenzoporphyrin (hereinafter "PhTBP") compounds. Preferred PhTBP compounds include substituted or unsubstituted tetraphenyltetrabenzoporphyrin (hereinafter "TTPhTBP") compounds, including mesotetraphenyltetrabenzoporphyrin (hereinafter "m-TPhTBP") compounds, which have the following formula:

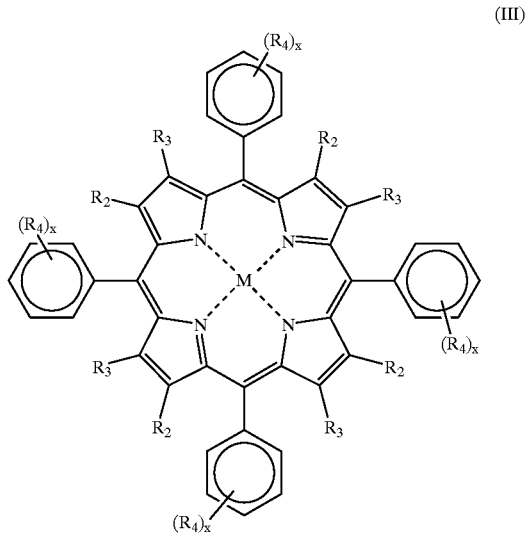

(III)

where $R_2$, $R_3$ and M are as defined above, $R_4$ is a substituent group, and x is an integer from 0 to 3. Particularly preferred TPhTBP compounds are substituted compounds of formula III where x is an integer from 1 to 3.

In connection with the preferred substituted compounds of the invention, Applicants have found that substituent groups impart desirable properties to the compounds. For example, compounds which comprise substituent groups are characterized by solubility in polar solvents, including aprotic solvents, such as dimethylformamide (DMF), acetone and chloroform ($CHCl_3$), and protic solvents, such as water. The degree of substitution and the nature of the substituent groups may be tailored to obtain the desired degree of solubility and in the desired solvent or solvent mixture.

The substituent groups are preferably substituted on the chromophobe portion of the compounds of the invention. The term "chromophobe portion" includes, for example, the atoms in the compound of formula I which are immediate to the porphyrin moiety, as well as the $R_1$, $R_2$ and $R_3$ groups. Preferably, the substituent groups do not negatively affect or alter the absorbance and/or emission characteristics of the chromophores.

Particularly preferred phosphorescent oxygen sensors for use in the method and apparatus of this invention include Pd-tetrabenzoporphyrin and Pd-meso-tetra-(4-carboxyphenyl) phosphine.

Also preferred for use in this invention are highly soluble phosphorescent probes suitable for measurements of oxygen in tissue of animals and humans. The inventive probes are surrounded by an inert globular structure, an example of which is derivatized PdTBD surrounded by three-dimensional supramolecular structure known as a dendrimer.

As is well known, one of the most effective methods to build a three-dimensional supramolecular structure around a functionalized core, such as a derivitized phosphor, is by dendritic polymer growth. Dendrimers are three-dimensional supramolecular radial symmetrical molecules comprised as an initiator core, such as nitrogen, polyfunctional amines such as ethylenediamine, or in the present invention the oxygen-measuring phosphors, with interior layers attached to the core which are comprised of, for example, three or four arms with each arm being composed of repeating units, and with the number of repeating units in each arm considered to be a generation of the dendrimer. The outermost generation typically contains terminal functional groups, such as a primary amine attached to the outermost generation. The size and shape of the dendrimer molecule, and the functional groups present therein can be controlled by the choice of the initiator core, the number of generations, and the nature of the repeating units employed at each generation. For example, the chemical functionality of the repeating units in the interior layers can be, amidoamines, such as diethylene diimine, and with terminal functionalities, such as, for example, amino groups, hydroxyl groups, carboxylic acid groups, carboxylates and the like. See URDEA et al., *Science* 261: 534 (1993) and FRECHET, 263: 1710–1715 (1994). Therefore, dendrimers are combinations of monomeric units which allow branching at each step of polymerization. As shown, for example, by BLUMEN et al., *Angewandte Chemie, Int.,* Ed. Eng. 29: 113–125 (1990), dendrimers tend to form globular structures with increasing numbers of monomeric units, which eventually will cover the centralized functional entity or compound. See also, for example, WINNIK et al., U.S. Pat. No. 5,256,193.

At least two methods are known for the synthesis of dendrimer polymeric structures: the convergent and divergent growth approaches, respectively. Both are contemplated for use in the present invention.

In the convergent dendrimer synthetic route, polymer synthesis is initiated from the periphery and ends by linking branched fragments to a central core. For a detailed description of the convergent synthetic method, see Hawker et al., *J. Am. Chem. Soc.* 114: 8405–8413 (1992), WOOLEY et al., *J. Chem. Soc.,* Perkin Trans. 1:1059–1076 (1991), and FRECHET et al., U.S. Pat. No. 5,041,516, all of which are incorporated herein by reference.

It has recently been reported that the convergent synthetic route is useful in the modification of porphyrins, i.e., producing a dendritic molecule with a core having photochemical functionality. See JIN et al., *J. Chem. Soc. Chem. Commun.* 1260–1262 (1993). This reference describes measuring quenching of fluorescence of a Zn porphyrin encapsulated in a dendritic cage, and that the dendrimer polymeric structure provides good protection for the porphyrin core, serving as a barrier for large molecules while allowing access to smaller species.

The more typically used divergent synthetic method employs a reverse order of synthesis which involves an initial reaction of a monomer with an initiator core, followed by successive reaction of the resulting functional groups with a difunctional compound, such as a diamine, to provide the next generation of reactive amino groups such that layers of monomeric units are added to a central core sequentially until the desired degree of branching is achieved. A detailed explanation of this method can be found, for example, in TOMALIA et al., *Angewandte Chemie, Int.,* Ed. Eng. 29: 138–175 (1990) and TOMALIA et al., *Macromolecules* 19: 2466–2468 (1986), which are also incorporated by reference herein.

Other references relating to dendritic macromolecules and their methods of production can be found in U.S. Pat. Nos. 5,418,301; 4,568,737; 5,393,795; 5,256,193; 5,393,797; 5,393,795; 5,393,797; 5,098,475; 5,041,516 and 4,568,737, the entire disclosures of which are incorporated herein by reference.

As described below, in one aspect of this invention, one-, two-, and three-layer polyglutamate dendritic cages synthesized divergently around novel derivatized metallo extended porphyrin oxygen-measuring phosphor compounds results in phosphors which are highly water-soluble in a wide pH range; excretable from the blood of mammals (mice) by filtration thereof through the kidney; and display narrow distribution of phosphorescence lifetimes in deoxygenated water solutions.

As further shown below, the combination of the novel phosphor derivatives with dendrimers which are used as the phosphor's surrounding environment, provides a novel class of phosphorescent probes for accurate and reliable 3-dimensional oxygen measurements in human and animal tissue in accordance with this invention.

The preparation of the phosphorescent oxygen probe dendrimers is illustrated below by a preferred synthetic embodiment. First, synthesis of PdTBP derivatives with chemically active functional groups is carried out to allow for further addition of dendritic fragments. Next, the actual layer-by-layer divergent growth of the dendrimer polymeric structure around the porphyrin core is accomplished to form the completed probe.

An alternate embodiment of convergent synthesis of the branched dendritic fragments, followed by attachment to a control porphyrin moiety is also contemplated.

Functionalizing a (Pd)TBP into (Pd)MCTBP

TBP and tetraphenyltetrabenzoporphrins (TPTBP) for use in this invention can be synthesized by the template condensation of potassium phthalimide with phenylacetate in the presence of Zn salts, according to the method reported by KOPRANENKOV, *J. Gen. Chem.* (Russ.) 51: 2165–2168 (1981) and ICHIMURA, *Inorg. Chem. Acta.* 182: 83–86 (1991). Tetratoluyltetrabenzoporphyrin can also be synthesized in approximately 10% yield by using 4-methylphenylacetate as a condensing agent. See, for example, Kopranenkov (1981). However, as both TBP and TPTBP compounds do not contain functional groups suitable for further modification, functional groups must be added to the formed TBP and TPTBP structures.

General approaches for modification of TBP and TPTBP in accordance with this invention include a) electrophilic substitution (chlorosulfation, nitration, etc.) of phenyl rings in TPTBP's, and b) electrophilic substitution, such as nitration, of meso-positions of non-substituted TBP followed by reduction and attachment of 1,3,5,-tricarboxylic acid fragments.

Figure 4:
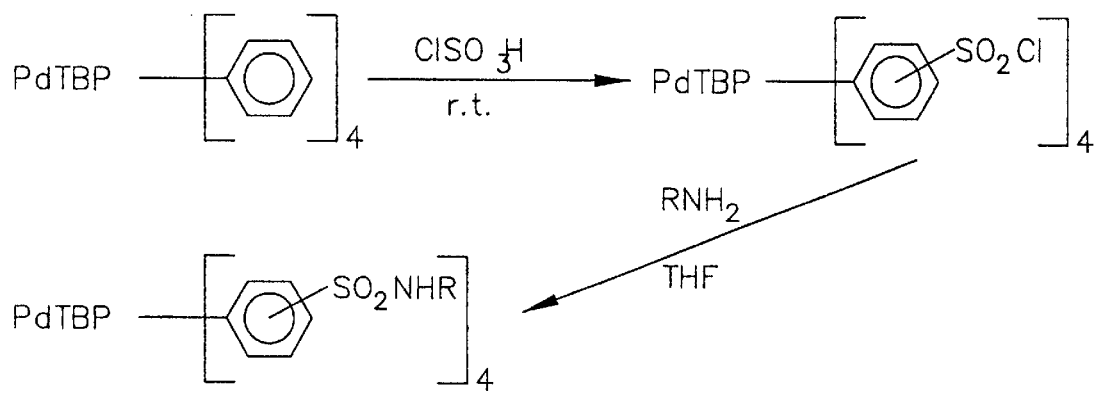
FIG. 4 illustrates an exemplary embodiment for the production of PdTBP and PdTPTPB functionalized derivatives, for initiating divergent dendrimer growth.

It is known that phenyl rings of TPTBP and PdTPTBP are most active in electrophilic substitution reaction. See, for example, VINOGRADOV and WILSON, *J. Chem. Soc., Perkin Trans.* 2: 103–111 (1995). Such reactions, however, are not always very selective and can lead to non-selectively modified probes, with substitution occurring in either the orth. or para-positions of phenyl substituents, with the resulting production of a variety of regio- and stereo-isomers which are present in the reaction products. As exemplified below in FIG. 4, chlorosulfation of PdTPTBP leads to a mixture of tetra substituted chlorosulfonate-PdTPBP, each of which can then react with different amines to initiate divergent dendrimer growth.

It has also been shown that PdTPTBP can be readily chlorosulfated and converted into the corresponding sulfonamide with aminopolyethyleneglycols. See VINOGRADOV and WILSON (1995).

Figure 5:
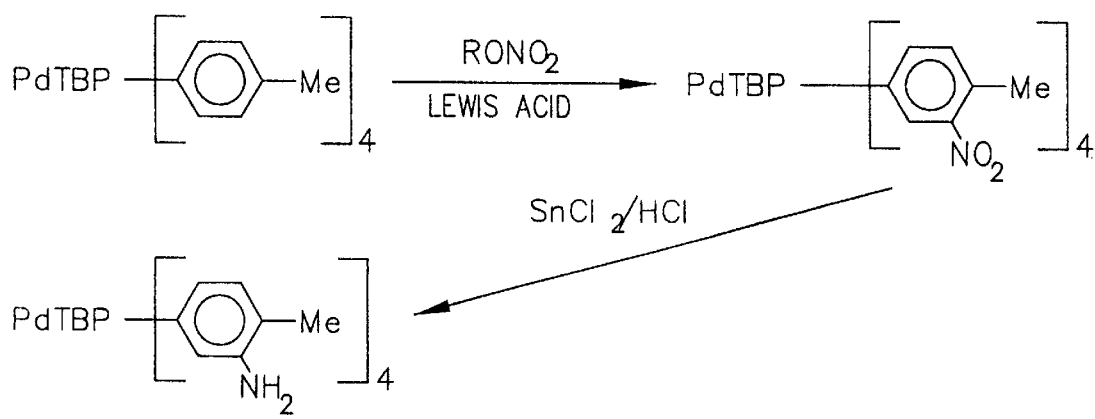
FIG. 5 illustrates another exemplary embodiment for the production of PdTBP and PdTPTBP functionalized derivatives for initiating divergent dendrimer growth.

In accordance with this invention, it is also contemplated that the employ of phenyl rings substituted with methyl groups will significantly decrease the number of isomers formed in electrophilic substitution due to stearic restrictions, especially when soft electrophiles are used for modification, thereby increasing selectivity. Therefore, in accordance with this invention it is contemplated that nitration of Pd tetratoluyltetrabenzoporphyrin with agents such as esters of nitric acid in presence of weak Lewis acids such as $LnCl_3$, $ZnCl_2$ or zeolites will lead to only one regioisomer, Pd tetra(4-methyl-3-nitrophenyl) tetrabenzoporphyrin. This can then be reduced to the corresponding amino derivative (FIG. 5). Separation of the stereoisomers can be performed chromatographically and methods have been described previously for meta- and orth-tetra-aminophenylporphyrins. See ROSE "Large-scale preparation of , β, ', β'-atropoisomer of meso-tetrakis (0-aminophenyl) porphyrin, *J. Org. Chem.*, 58:5030–5031 (1993).

Figure 6A:
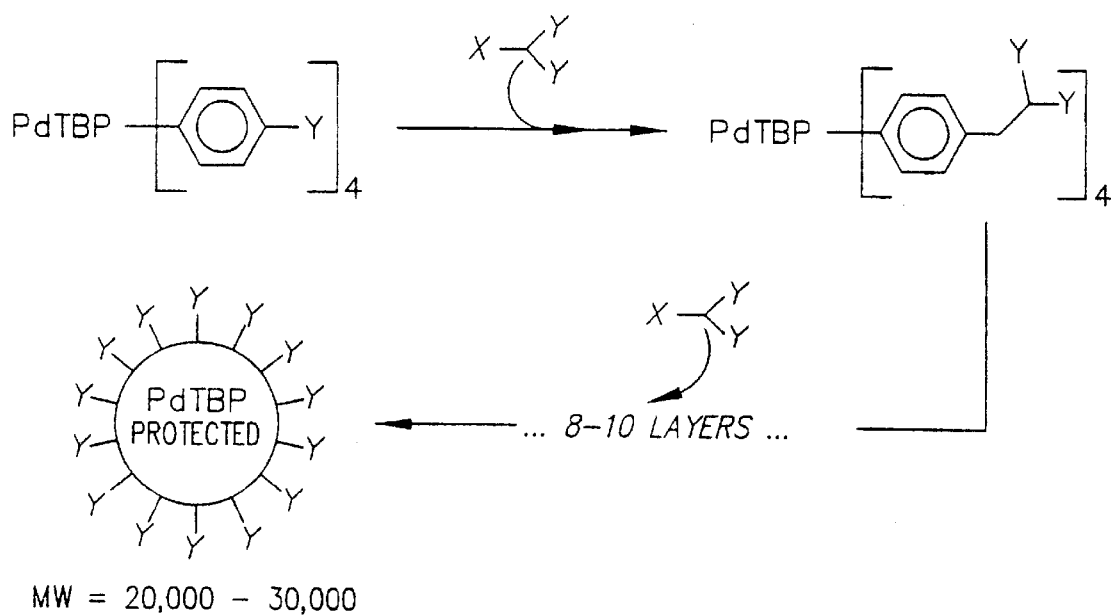
FIG. 6A illustrates the production of dendrimer growth on a core functionalized porphyrin with functional groups located at the para-positions of meso-phenyl rings.

Molecular-mechanics simulations carried out with MacroModel (Unix Version 3.5, MM2 force field) in accordance with that reported in MOHAMADI et al., *J. Comput. Chem.* 11: 440 (1990) show that 6–10 layers of monomeric units, such as glutamates, are preferably added to a porphyrin if the initial functional groups are located at the para-positions of meso-phenyl rings to desirably achieve good protection of the central porphyrin fragment using the divergent synthetic approach (see FIG. 6A). This leads to molecules with molecular weights of about 14,000–30,000 Daltons. However, such large species might not be very useful in practice because of difficulties in excretion from the blood stream.

Figure 6B:
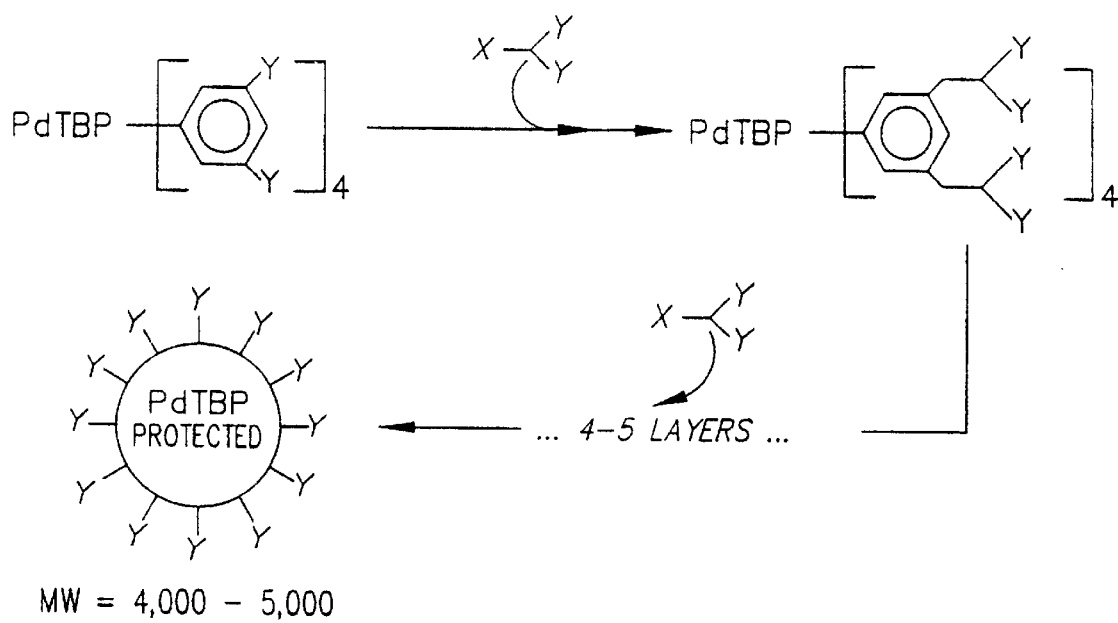
FIG. 6B illustrates the production of dendrimer growth on a core functionalized porphyrin with functional groups located at the meta-positions of meso-phenyl rings.

Further experimental data has shown that three layers decreases the oxygen quenching constant from near $2 \times 10^3$ $Torr^{-1}$ $sec^{-1}$ to about 750 $Torr^{-1}$ $sec^{-1}$. The latter is similar to that observed for the porphyrin bound to albumin and is suitable for measurements in vivo. Thus, it is preferable that up to four layers of glutamate will be sufficient for achieving an optimized oxygen probe. In any case, molecular modeling shows that if dendrimer growth starts from the meta-positions, globular structures form much faster and only three to five layers of monomers are needed for generation of a fully globular structure (see FIG. 6B). In this case, the molecular weight of the probe molecules will be between about 4,000 and 5,000 Daltons, which is a desirable size for good penetration through the kidney filters. Thus, it is preferred that functional groups be introduced selectively into the meta-positions of the meso-phenyl substituents.

However, it is contemplated that the porphyrin moiety will direct electrophilic substitution to the para- and orth- positions of the phenyl rings.

Figure 7A:
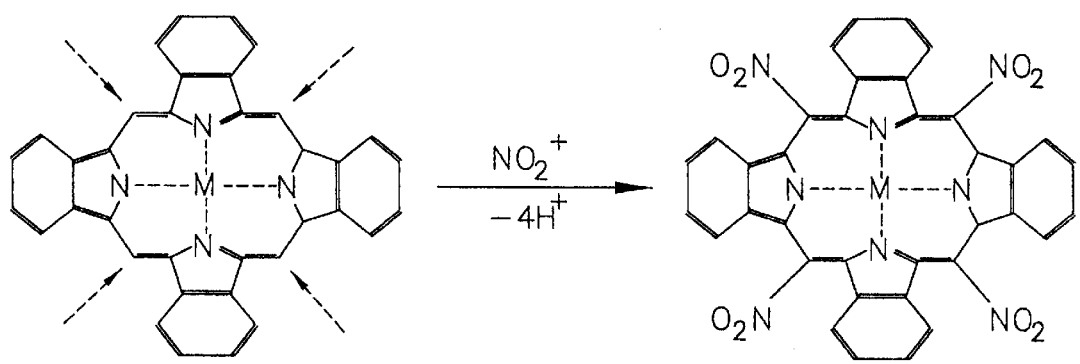
FIG. 7A illustrates a preferred embodiment of the invention of the production of a functionalized PdTBP with meta- (or psuedo meta-) functional groups by direct nitration of non-substituted TBP into meso-positions to produce (Pd) tetraminotetrabenzoporphyrin (PdTNTBP).

In a further embodiment of this invention, another reaction pathway to achieve formation of PdTBP with meta- (or pseudo meta-) functional groups is provided. This reaction is based on the direct nitration of non-substituted TBP into meso-positions, (see FIG. 7A). As shown in FIG. 7A, the arrows indicate the most probable direction for electrophilic attack. Direct nitration of porphyrins is known. See DRACH et al., *J. Org. Chem.* 39: 3282–3284 (1974) and BONNET et al., *J. Org. Chem.* 30: 2791–2798 (1965). The direct nitration of ZnTBP is also known. See KOPRANENKOV et al., *Chem. Heter. Comp. (Russ.)*, 960–964 (1986). As shown in this reference, by using $HNO_3$/acetic acid and $HNO_2$/trifluoroacetic acid, up to four nitro groups can be introduced into the meso-positions of TBP cycle with yields of up to 11%.

It is also contemplated in this invention that strong ionic nitrating agents, such as, for example, $BF_4NO_2$ or highly activated covalent nitrating systems, such as, for example, AcONO$_2$/BF$_3$.ET$_2$O and RONO$_2$/TiCl$_4$ be employed to increase both overall yield of nitration and the relative yield of tetranitrotetrabenzoporphyrin (TNTBP). Nitration can be carried out at the earliest state of transformation when TBP is present as its Zn complex.

Figure 7B:
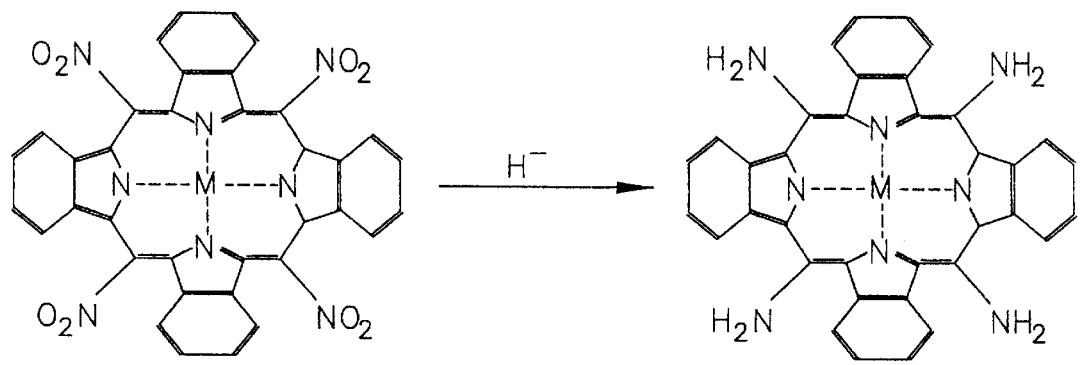
FIG. 7B further illustrates the preferred embodiment of the functionalized core porphyrin of FIG. 4A by the transformation of (Pd)TNTBP into the corresponding tetramino-tetrabenzoporphyrin (TATBP or PdTATBP).

It has also been found that Zn tetranitrotetrabenzopophyrins (meso-TNTBP) can be easily demetallated by using AcOH/H$_3$PO$_4$ and that the insertion of Pd into TNTBP proceeds faster than into non-substituted TBP, which is due to increased non-planarity of the tetranitrated macrocycle, as confirmed using molecular-mechanics calculations (MacroModel V.3.5, MM2 force field). The reduction of TNTBP (or PdTNTBP) into corresponding tetraaminotetrabenzoporphyrin (TATBP or PdTATBP) is shown in FIG. 7B. In accordance with this invention, the resulting TATBP can be produced in good yield by preferably employing systems with increasing reducing activity, such as Zn/HCl, SnCl$_2$/AcOH, Na/MeOH, NaBH$_4$/MeOH, LiAlH$_4$/THF.

Figure 7C:
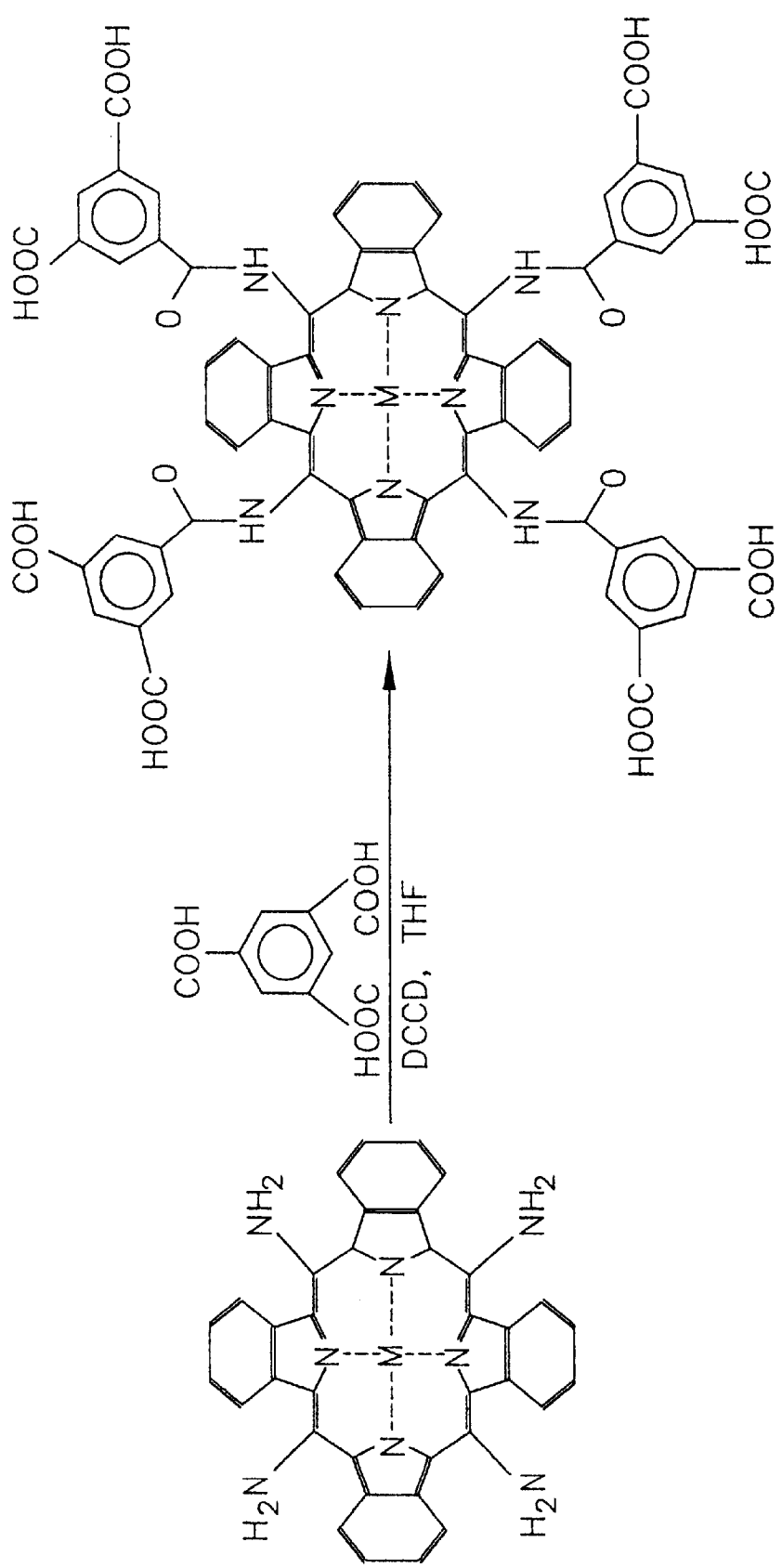
FIG. 7C further illustrates a preferred embodiment of the invention by additional functionalization of TATBP or PdTATBP in FIG. 5B with 1, 3, 5 -benzenetricarboxylic acid to produce (Pd) metacarboxytetra-benzoporphyrin (MCTBP or PdMCTBP).

After formation of TATBP, further derivatization can be achieved by any of several methods employing high reactivity of the amino groups. A preferred method is amide formation between 1,3,5-benzene-tricarboxylic acid and TATBP (or PdTATBP) carried out in the presence of dicyclohehylcarbodiimide (DCCD) to produce a TBP containing pseudo meso-phenyl substituents with meta-carboxyl groups, or as termed herein, metacarboxytetrabenzoporphyrin (MCTBP). In accordance with this preferred illustrative embodiment, MCTBP, or its Pd derivative, as shown below can be used as a core for dendritic polymer growth. See FIG. 7C.

In yet another aspect of this invention, a preferred direct synthesis of functionalized porphrins is provided which leads directly to substituted TPTBP with chemically active functionalities and suitable as a core for dendritic polymer growth. As discussed hereinabove, tetrabenzoporphrins, TBP, and tetraphenyltetrabenzoporphyrins, TPTBP, are generally synthesized by template condensation of potassium phthalimide with sodium acetate or sodium phenylacetate in the presence of Zn salts. However, due to the harsh conditions required for the template condensation, functional groups in either phthalimide or phenylacetic acid fragments usually do not survive. In accordance with the present invention, it has now been found that under modified conditions, meso-p-Br-phenyltetrabenzoporphyrins (PdTBrPTBP) and meso-p-Cl-phenyltetrabenzoporphrins (PdTClPTBP) can be synthesized directly from bromo-and chloro-phenylacetic acids. These compounds can then be converted to reactive functionalized TPTBP's by means of Pd-catalyzed cross-coupling and catalytic carbonylation. For example, with Pd catalysis, PdTPhTBP's containing Br-substituents can be converted into corresponding carboxyl compounds as follows:

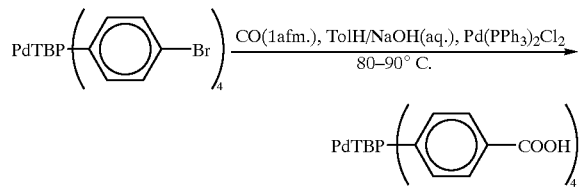

Catalytic reactions, including carbonylation and cross-coupling, for transformation of aryl halides into more reactive aryl derivatives are discussed in COLQUHOUN et al., "Carbonylation: direct synthesis of carbonyl compounds", *Plenum Press,* New York, (1991) and HECK, "Palladium reagents in organic synthesis", *Academic Press,* New York, (1985).

Building a Dendrimer Around (Pd)MCTBP

Dendrimers can be grown from any multi-substituted core, such as a multi-substituted porphyrins, with their different respective properties merging with increase of polymer layers. A divergent dendritic growth scheme example in accordance with this invention is conveniently shown as built around that of a functional (Pd)MCTBP core. While a convergent growth scheme is also contemplated, divergent growth is preferred as it appears to allow for more economical use of PdMCTBP and for more convenient measurements of optical and quenching properties on each step of modification. Once the necessary protection of the porphyrin is achieved, as measured by oxygen quenching constant, the addition of extra layers is not necessary; a finished probe molecule having the desired optimal size is easily synthesized.

In the present invention, any one of several known monomeric units for the formation of divergent dendrimers are useful, such as, for example, as described in U.S. Pat. Nos. 4,507,466; 4,631,337; 4,558,120; 4,568,737 and 4,587,329, and in TOMALIA, *Angewandte Chemie, Int. Ed. Eng.* 29:138–175 (1990) and TOMALIA, *Macromolecules,* 19:2466–2468 (1986), the entire disclosures of which are incorporated herein by reference. Other monomeric units suitable for use in the present invention for carrying dendrimer growth around a porphyrin core can be, for example, ∝, ε-L-lysine described in U.S. Pat. No. 4,289,872 and 1,3-diaminopropan-2-ol in combination with suitable , β-unsaturated carbonyl compound, such as described in TWYMAN et al., Perkin Trans. 1:407–411 (1994), which are incorporated herein by reference.

Figure 8:
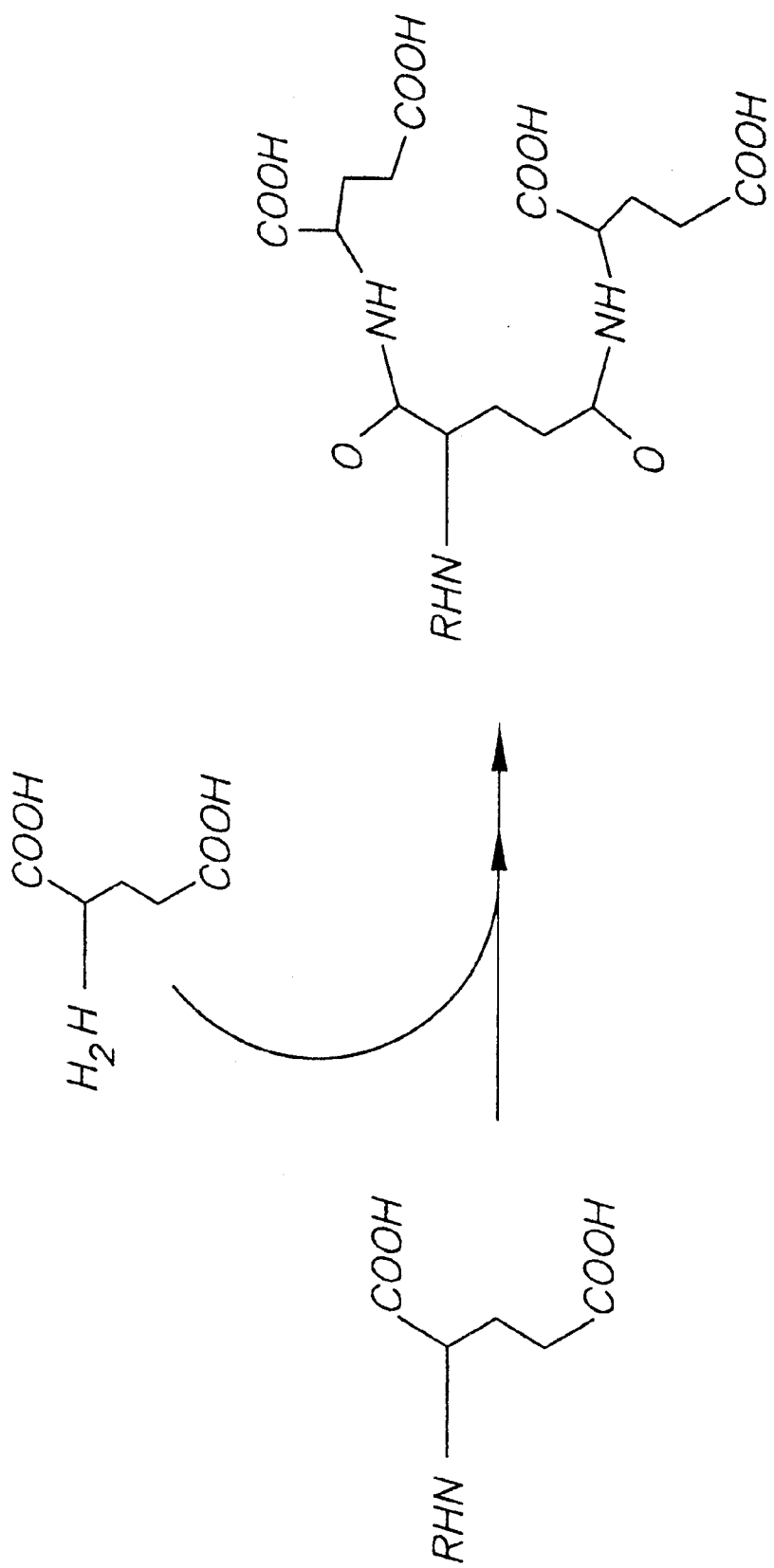
FIG. 8 illustrates the occurrence of branching in a divergent dendrimer growth mode through amide linkages formed using glutamic acid.

In a preferred embodiment of the invention, glutamic acid diallyl ester (diallylglutamate) is employed as a monomeric unit for the modification of PdMCTBP. Diallylglutamate has two protected carboxylic groups and one amino group as shown in FIG. 8. Branching and dendritic polymer formation occurs through formation of amide linkages of each step of polymer formation. It is noted that the reaction scheme in FIG. 8 is drawn for simplicity reasons, and only illustrates non-protected glutamic acid, and not diallyl-glutamate.

The reaction between the carboxyl functionalities of the porphyrin PdMCTBP (Pd-meso-tetra-(4-carboxyphenyl) porphyrin) and diallylglutamate proceeds smoothly in THF at room temperature in the presence of a 1.2 molar excess of DCCD, to produce the corresponding tetraamide in practically quantitative yield.

Figure 9:
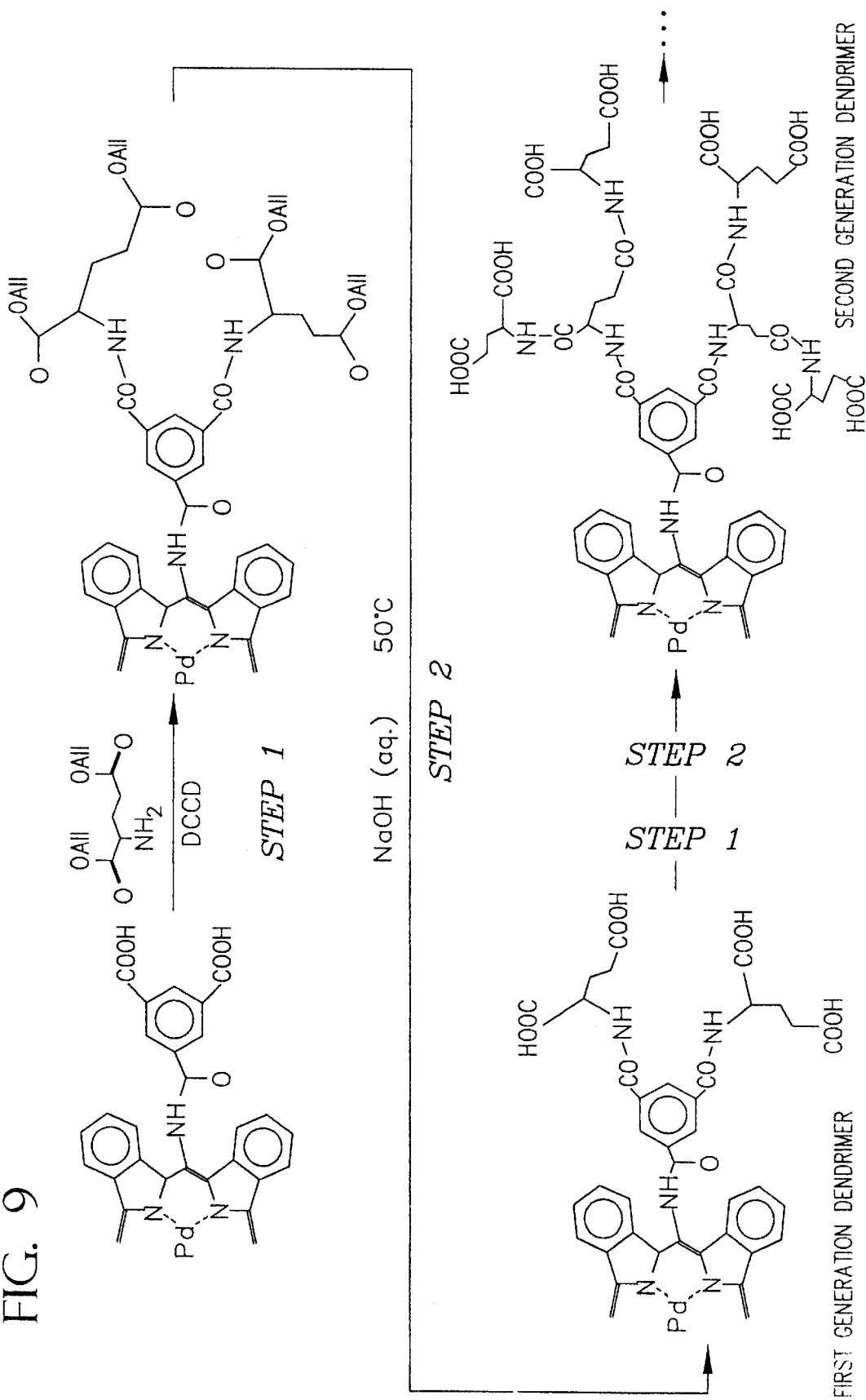
FIG. 9 illustrates a preferred embodiment of the invention of divergent dendrimer growth through two generations using MCTBP or its derivative PdMCTBP as a core porphyrin and diallylglutamate as a monomeric unit.

The allylic moiety on the introduced carboxylic groups can be readily removed by treatment of the ester with warm aqueous NaOH. Amide linkages are completely stable under these reaction conditions. Thus, hydrolysis gives porphyrin with twice as many carboxyl groups, which is ready for the addition of a new glutamate layer, or a second generation. The two first stages of the overall reaction process are shown in FIG. 9. Step 1 denotes amide linkage formation, while Step 2 denotes base catalyzed hydrolysis of the allyl ester protective groups. Purification of the final reaction product can be achieved using membrane filtration, dialysis and size exclusion chromatography, such as successfully employed for the purification of "caged" Zn porphyrin. See JIN et al., *J. Chem. Soc. Chem. Commun.* 1260–1262 (1993).

As mentioned above, other monomeric units can be employed for dendrimer formation. These units can have protected functional groups suitable for formation of ester or ether linkages, such as frequently used in convergent dendrimer growth schemes and which are described in HAWKER, *J. Am. Chem. Soc.* 112:7683–7647 (1990); and *J. Am. Chem. Soc.* 114: 8405–8413 (1992) WOOLEY, *J. Chem. Soc.*, 1:1059–1076, Perkin Trans. 1 (1991)(1992), the entire disclosures of which are incorporated herein by reference.

Figure 10:
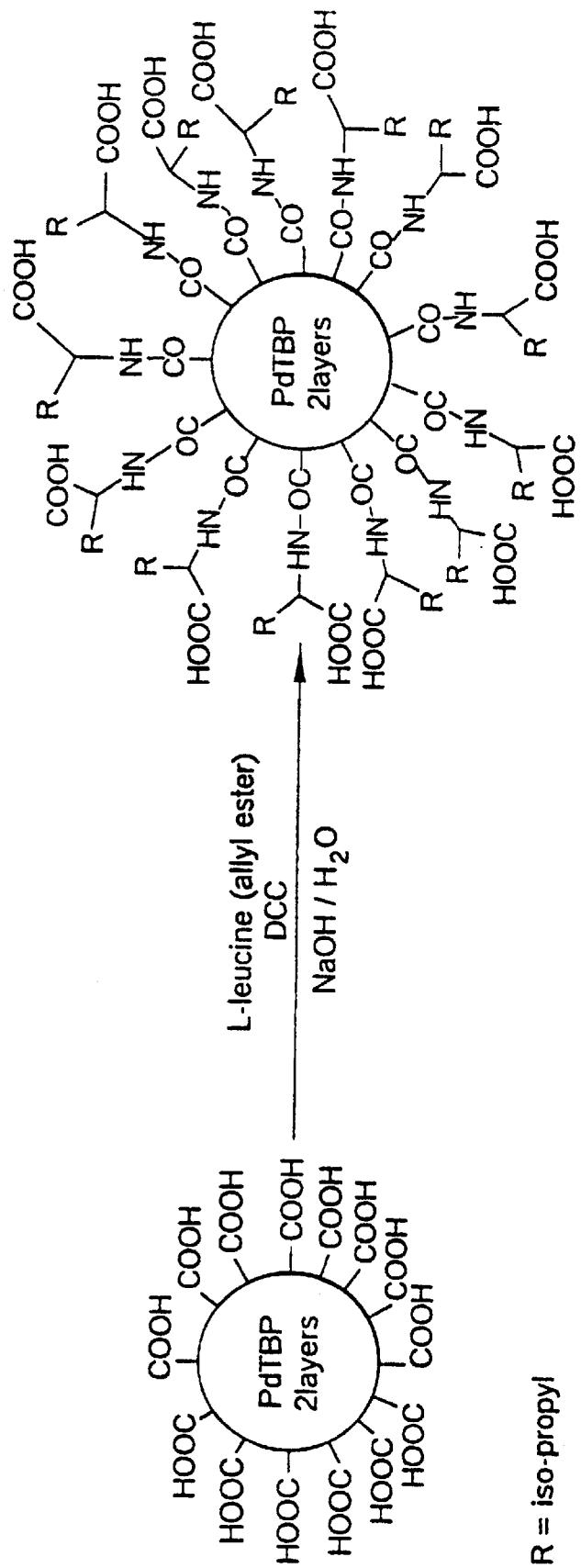
FIG. 10 illustrates a preferred embodiment of the invention of the modification of an outer layer of dendritic porphyrin.
Figure 11:
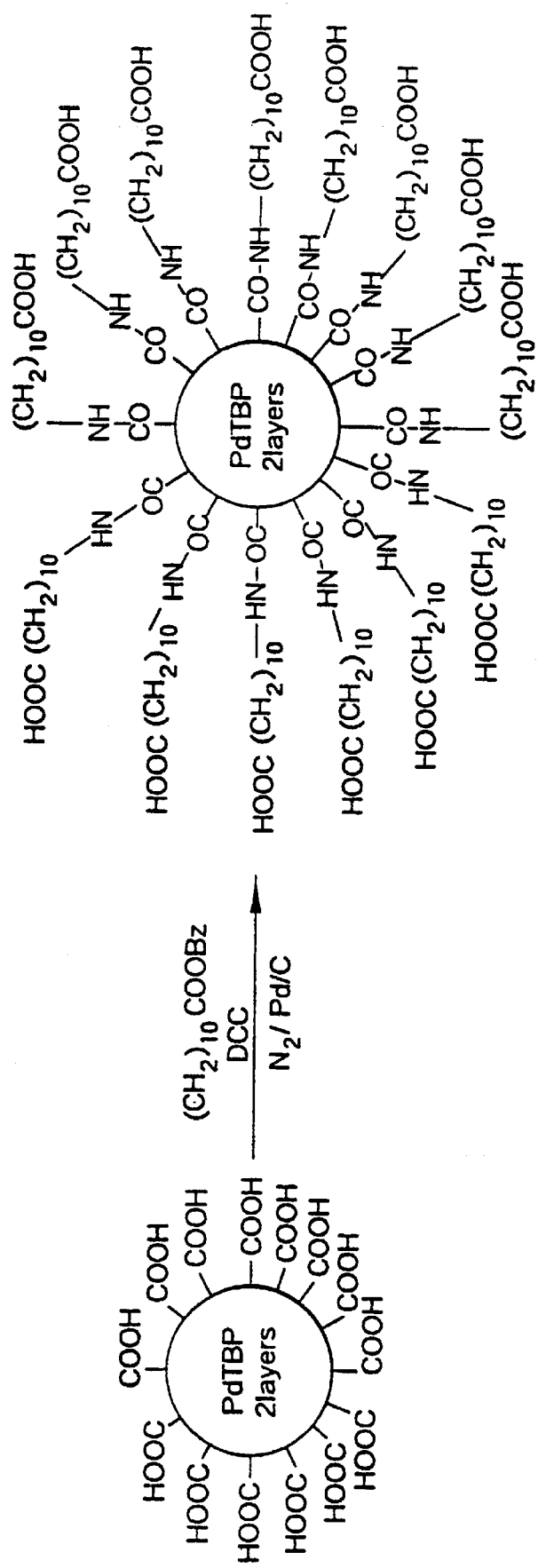
FIG. 11 illustrates another preferred embodiment of the invention of the modification of an outer layer of dendritic porphyrin.

In a further aspect of the present invention, it has been found that modification of the outer layer of dendritic porphyrins with various hydrophobic groups improves protection of core porphyrins. While not wishing to limit any aspect or portion of this invention to theory, it is thought that the addition of surface hydrophobic groups causes formation of more compact structures in water solutions, thereby decreasing oxygen quenching constants. It is also thought that hydrophobic interactions within relatively loosely packed polyamide dendrimer causes it to shrink into smaller ball-like structures of high density which prevent or at least decrease the rate of diffusion of oxygen molecules to the porphyrin core. As illustrated, for example in FIG. 10, significant protection of porphyrin can be achieved when 2-layered polyglutamate dendrimer is surface modified with L-leucine. Furthermore, lower quenching constants are observed for 2-layered polyglutamate modified with sixteen 11-aminoundecanoic acid residues. See FIG. 11.

What is claimed is:

1. A detection device for tissue oxygen measurement in animals and humans comprising:
    an array of fiber optic means effective for transmitting excitation light;
    an array of fiber optic means effective for collecting and transmitting emitted phosphorescent light;
    an array of phosphorescent detection means;
    wherein the arrays form a matrix means, by which pulses of excitation light are sequentially introduced from, and phosphorescence detected at, a plurality of sites within the matrix.

2. The device of claim 1, wherein tissue oxygen is measured two-dimensionally.

3. The method of claim 1, wherein tissue oxygen is measured three-dimensionally.

4. The detection device of claim 1, wherein said device is used in conjunction with an oxygen-quenchable phosphorescence emitting oxygen sensor.

5. The detection device of claim 2, wherein said oxygen sensor comprises an absorption band at a wavelength of greater than about 400 nm.

6. The detection device of claim 5, wherein said sensor comprises an emission band at a wavelength of greater than about 400 nm.

7. The detection device of claim 6, wherein said absorption and emission bands are located in the range from about 400 nm to about 1000 nm.

8. The detection device of claim 5, wherein said absorption band ranges from about 400 to about 700 nm.

9. The device of claim 4, wherein said sensor comprises porphyrin.

10. The detection device of claim 9, wherein said porphyrin comprises metalloporphyrin.

11. The detection device of claim 10, comprising an oxygen sensor compound which is capable of phosphorescing and which has the formula:

wherein:

$R_1$ is substituted or unsubstituted aryl;

$R_2$ and $R_3$ are independently hydrogen or are linked together to form substituted or unsubstituted aryl; and M is $H_2$ or a metal.

12. The detection device of claim 11, wherein the oxygen sensor compound M is a metal selected from the group consisting of Zn, Al, Sn, Y, La, Lu, Pd, Pt and derivatives thereof.

13. The detection device of claim 12, wherein the derivatives of the oxygen sensor compound comprise LuOH, YOH, LaOH or AlOH.

14. The detection device of claim 11, wherein $R_2$ and $R_3$ of the oxygen sensor compound are linked together to form an aryl system.

15. The detection device of claim 14, wherein the oxygen sensor compound of the aryl system comprises phenyl, naphthyl or anthryl.

16. The detection device of claim 15, wherein $R_1$ of the oxygen sensor compound comprises substituted phenyl.

17. The detection device of claim 16, wherein the oxygen sensor compound is Pd-meso-tetra-(4-carboxy-phenyl) porphine.

18. The detection device of claim 4, wherein oxygen measurement in human or animal tissue comprises a porphyrin chromophore capable of releasing absorbed energy as phosphorescent light and a dendrimer, and wherein the porphyrin chromophore comprises the core of the dendrimer.

19. The detection device of claim 18, wherein the absorption spectrum of the chromophore phosphorescent probe exhibits strong light absorption in the near infrared region of the spectrum, at which point on the spectrum, natural tissue chromophores exhibit relatively weak absorption.

20. The detection device of claim 18, wherein the absorption spectrum of the chromophore of the phosphorescent probe exhibits strong light absorption between 600 nm to about 720 nm.

21. The detection device of claim 18, wherein the absorption spectrum of the chromophore of the phosphorescent probe exhibits strong light absorption between 610 nm to about 720 nm.

22. The detection device of claim 18, wherein the porphyrin chromophore of the phosphorescent probe comprises a functionally derivatized metalloporphyrin.

23. The detection device of claim 22, wherein the formula for the functionally derivatized metalloporphyrin of the porphyrin chromophore of the phosphorescent probe is

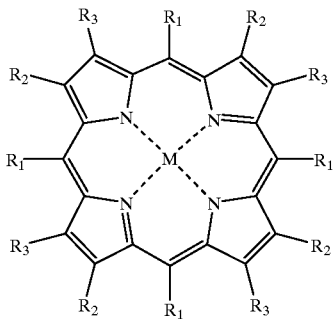

wherein $R_1$ is a hydrogen atom or a substituted or unsubstituted aryl; $R_2$ and $R_3$ are independently hydrogen or are linked together to form substituted or unsubstituted aryl; and M is $H_2$ or a metal.

24. The detection device of claim 23, wherein M of the metalloporphyrine compound is a metal selected from the group consisting of Zn, Al, Sn, Y, La, Lu, Pd, Pt and derivatives thereof.

25. The detection device of claim 22, wherein the porphyrin chromophore compound is selected from the group consisting of tetrabenzoporphyrin, tetranapthoporphyrin, tetraanthraporphyrin and derivatives thereof.

26. The detection device of claim 25, wherein a derivative of the porphyrin chromophore compound is a meso-tetraphenylated compound.

27. The detection device of claim 25, wherein the porphyrin chromophore compound is tetrabenzoporphyrin.

28. The detection device of claim 25, wherein the metal of the porphyrin chromophore compound is selected from the group consisting of Zn, Al, Sn, Y, La, Lu, Pd, Pt and derivatives thereof.

29. The detection device of claim 28, wherein the metalloporphyrin chromophore is tetraphenyltetrabenzoporphyrin.

30. The detection device of claim 28, wherein the metallopophyrin chromophore is (Lu) tetraphenyltetranapthoporphyrin.

31. The detection device of claim 28, wherein the metalloporphyrin chromophore compound is meso-tetra-(4-carboxylphenyl) porphyrin.

32. The detection device of claim 28, wherein the metallopophyrin chromophore compound is mesotetraphenyltetrabenzoporphyrin.

33. The detection device of claim 28, wherein the metalloporphyrin chromophore compound is a first, second, third, fourth or fifth generation dendrimer cages.

34. The detection device of claim 23, wherein the dendrimer of the metalloporphyrin chromophore compound comprises polyglutamate dendritic.

* * * * *